United States Patent [19]
Garrison et al.

[11] Patent Number: 5,849,005
[45] Date of Patent: Dec. 15, 1998

[54] METHOD AND APPARATUS FOR MINIMIZING THE RISK OF AIR EMBOLISM WHEN PERFORMING A PROCEDURE IN A PATIENT'S THORACIC CAVITY

[75] Inventors: Michi E. Garrison, Belmont; Brian S. Donlon, Los Altos Hills; Richard L. Mueller, Jr., Byron, all of Calif.

[73] Assignee: Heartport, Inc., Redwood City, Calif.

[21] Appl. No.: 585,871

[22] Filed: Jan. 16, 1996

Related U.S. Application Data

[63] Continuation-in-part of Ser. No. 485,600, Jun. 7, 1995, abandoned.
[51] Int. Cl.$^6$ .................................................... A61B 17/00
[52] U.S. Cl. ............................... 606/1; 604/26; 604/264
[58] Field of Search ................................. 604/23, 26, 48, 604/49, 43, 93, 104, 122, 264, 174; 128/207.14–16; 600/560; 606/1

[56] References Cited

U.S. PATENT DOCUMENTS

| | | |
|---|---|---|
| 3,409,013 | 11/1968 | Berry . |
| 4,042,979 | 8/1977 | Angell . |
| 4,048,992 | 9/1977 | Lindemann et al. ...................... 604/26 |
| 4,173,981 | 11/1979 | Mortensen . |
| 4,207,887 | 6/1980 | Hiltebrandt et al. ...................... 604/26 |
| 4,217,665 | 8/1980 | Bex et al. . |
| 4,489,446 | 12/1984 | Reed . |
| 4,617,933 | 10/1986 | Hasson . |
| 4,655,218 | 4/1987 | Kulik et al. . |
| 4,869,717 | 9/1989 | Adair ...................................... 604/26 |
| 4,917,698 | 4/1990 | Carpentier et al. . |
| 4,962,757 | 10/1990 | Stefan ..................................... 604/174 |
| 5,011,481 | 4/1991 | Myers et al. . |
| 5,032,128 | 7/1991 | Alonso . |
| 5,041,130 | 8/1991 | Cosgrove et al. . |
| 5,061,277 | 10/1991 | Carpentier et al. . |
| 5,064,431 | 11/1991 | Gilbertson et al. . |
| 5,104,407 | 4/1992 | Lam et al. . |
| 5,109,859 | 5/1992 | Jenkins . |
| 5,137,509 | 8/1992 | Freitas . |
| 5,139,478 | 8/1992 | Koninckx et al. ....................... 604/26 |
| 5,139,485 | 8/1992 | Smith et al. . |
| 5,188,619 | 2/1993 | Myers . |
| 5,197,979 | 3/1993 | Quintero et al. . |
| 5,199,944 | 4/1993 | Casmescu . |
| 5,201,880 | 4/1993 | Wright et al. . |
| 5,203,776 | 4/1993 | Durfee . |
| 5,246,419 | 9/1993 | Abster ..................................... 604/26 |

(List continued on next page.)

FOREIGN PATENT DOCUMENTS

| | | |
|---|---|---|
| 0 218 275 | 4/1987 | European Pat. Off. . |
| WO 93/20741 | 10/1993 | WIPO . |
| WO 93/20742 | 10/1993 | WIPO . |

OTHER PUBLICATIONS

Berreklouw et al. "Revival of Right Thoracotomy to Approach Atrioventricular Valves in Reoperations" *Thorac Cardiovasc Surgeon* (1984) 32:331–333.

Buckberg, G.D. "Strategies and logic of cardioplegic delivery to prevent, avoid, and reverse ischemic and reperfusion damage" *J. Thorac Cardiovasc Surg.* (1987) 93:127–139.

Cohn et al., "Right Thoracotomy, Femorofemoral Bypass, and Deep Hypothermia for Re–replacement of the Mitral Valve" *Ann Thorac Surg* (1989) 48:69–71.

(List continued on next page.)

*Primary Examiner*—Mark Bockelman
*Attorney, Agent, or Firm*—Jeffry J. Grainger; Jens E. Hoekendijk

[57] ABSTRACT

An apparatus for minimizing the risk of air embolism includes an instrument delivery member 2 having a gas outlet 38 for delivering gas into a patient's thoracic cavity. The gas is directed across an opening 48 in the instrument delivery member 2 to help retain the gas in the patient's thoracic cavity. The gas is preferably carbon dioxide which is more soluble in blood than air which will thereby decrease the likelihood of the patient receiving an embolism due to trapped air in the patient's heart and great vessels after surgery.

10 Claims, 12 Drawing Sheets

U.S. PATENT DOCUMENTS

| | | |
|---|---|---|
| 5,250,038 | 10/1993 | Melker et al. . |
| 5,258,021 | 11/1993 | Duran . |
| 5,290,300 | 3/1994 | Cosgrove et al. . |
| 5,306,296 | 4/1994 | Wright et al. . |
| 5,308,320 | 5/1994 | Safar et al. . |
| 5,332,402 | 7/1994 | Teitelbaum . |
| 5,350,420 | 9/1994 | Cosgrove et al. . |
| 5,370,631 | 12/1994 | Zhong . |
| 5,376,112 | 12/1994 | Duran . |
| 5,383,860 | 1/1995 | Lau .......................................... 604/164 |
| 5,391,156 | 2/1995 | Hildwein et al. . |
| 5,403,305 | 4/1995 | Sauter et al. . |
| 5,419,314 | 5/1995 | Christopher ......................... 128/207.14 |
| 5,474,533 | 12/1995 | Ward et al. ................................ 604/26 |
| 5,531,758 | 7/1996 | Uschold et al. .......................... 604/167 |

OTHER PUBLICATIONS

Coltharp, William H., et al. "Videothorascopy . . . " *Ann Thorac Surg* (1992) 53:776–9.

Cosgrove, D.M. "Management of the Calcified Aorta: An Alternative Method of Occlusion" *Ann Thorac Surg.* (1983) 36:718–719.

H.G. Erath, Jr. and William S. Stoney, Jr. "Balloon Catheter Occlusion of the Ascending Aorta" *Ann Thorac Surg.* (1983) 35:560–561.

J.H. Foster and J.B. Threlkel "Proximal Control of Aorta with a Balloon Catheter" *Surg. Gynecology & Obstetrics* (1971) pp. 693–694.

Fundaro et al. "Towards an easier and safer reoperation of the atrioventricular valves. The right anterolateral thoracotomy approach without pericardial disssection" *J. Cardiovasc Sur* (1989) 30:779–781.

Jamieson, W.R. Eric "Modern Cardiac Valve Devices–Bioprostheses and Mechanical Prostheses" *J Card Surg* (1993) 8:89–98.

Landreneau et al., "Video–Assisted Thoracic Surgery . . . " *Ann Thorac Surg* (1992) 54:800–7.

Mack et al. "Present Role of Thoracoscopy in the Diagnosis and Treatment of Diseases of the Chest" *Ann Thorac Surg* (1992) 54:403–9.

Magovern, George J. "Sutureless Aortic and Mitral Prosthetic Valves" *J Thoracic and Cardiovasc Surg* (1964) 48(3):346–361.

Meditech®, Instructions for Use, Occlusion Balloon catheters Rev. Mar. 1991, p. 1–7.

Ozuner et al. "Creation of a Pericardial Window Using Thoracoscopic Techniques" *Surg. Gynecology & Obstetrics* (1992) 175:69–71.

Peters, W.S. "Minimally invasive cardiac surgery by cardioscopy" *AustralAs J. Cardiac Thorac Surg.* 1993;2(3):152–154.

Sakaguchi et al. "Aortic Valve Replacement and Coronary Artery Bypass" *J. Japanese Assoc. for Thoracic Surgery* (1993) 41(6):1063–1068. Abstract only Mar. 13, 1998.

Tribble et al. "Anterolateral Thoracotomy as an Alternative to Repeat Median Sternotomy for Replacement of the Mitral Valve" *Ann Thorac Surg,* 1987:43:380–382.

Wakabayashi, Akio "Expanded Applications of Diagnostic and Therapeutic Thoracoscopy" *J Thorac and Cardiovasc Surg,* 1991;102:721–3.

Yamaguchi et al. "A case of a reoperation using a balloon catheter with blocked pars acendes aortae" *Kyobu Geka,* 1991;42(11):961–964.

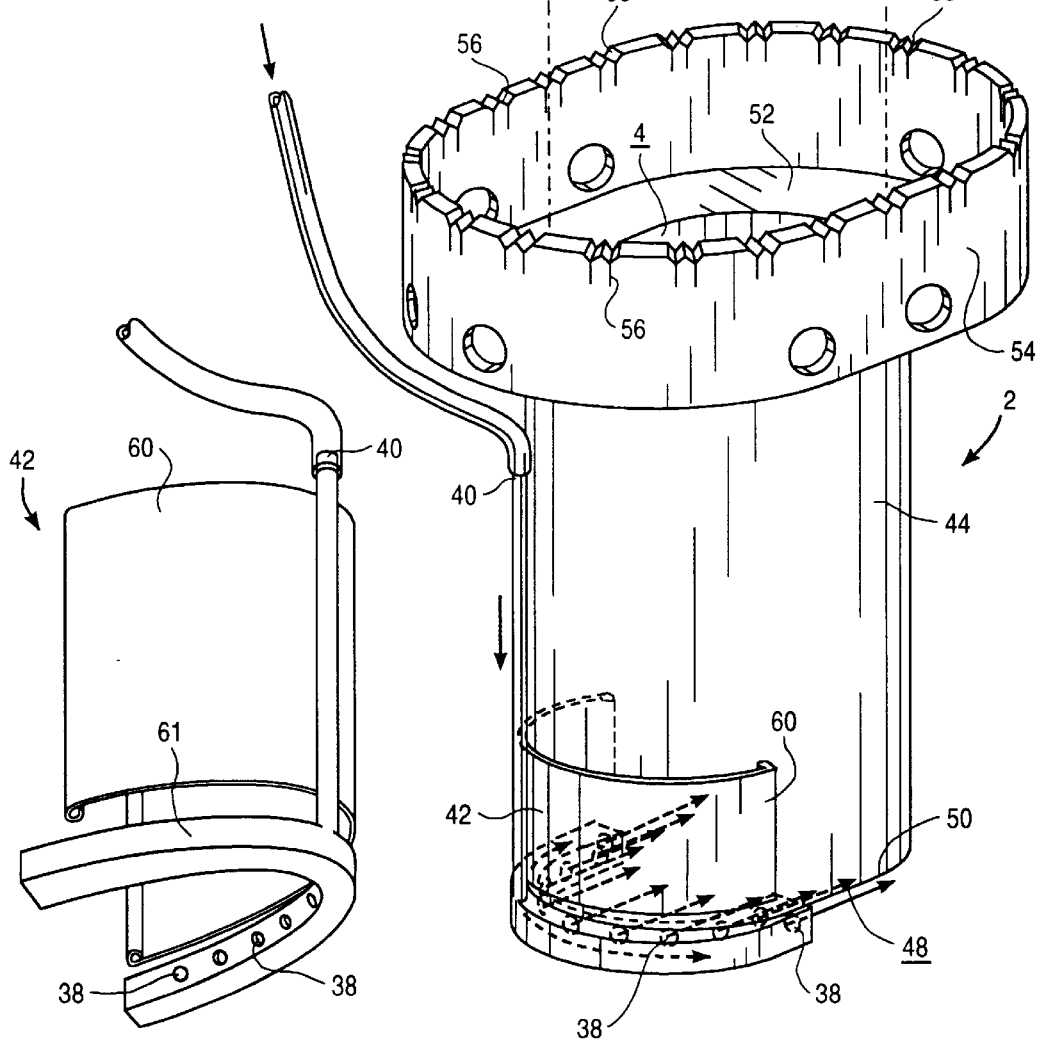

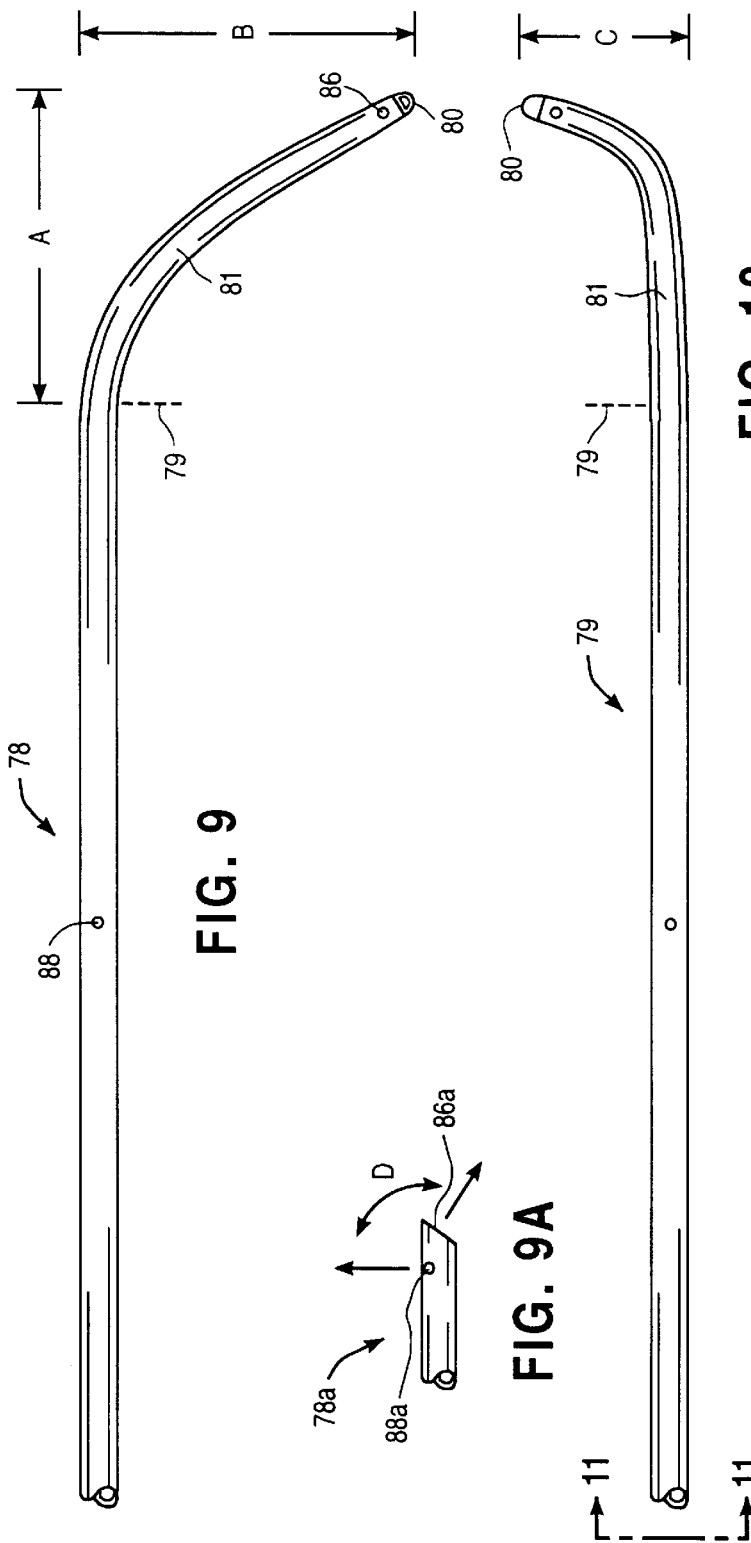
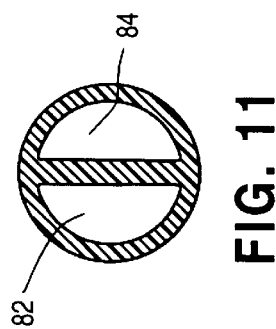

METHOD AND APPARATUS FOR MINIMIZING THE RISK OF AIR EMBOLISM WHEN PERFORMING A PROCEDURE IN A PATIENT'S THORACIC CAVITY

CROSS-REFERENCE TO RELATED APPLICATIONS

This application is a continuation-in-part of U.S. patent application Ser. No. 08/485,600, filed Jun. 7, 1995 now abandoned by inventors Garrison et al., and is related to U.S. patent application Ser. No. 08/415,366, filed Mar. 30, 1995 now abandoned by inventors Stevens et al., the complete disclosures of which are hereby incorporated by reference for all purposes.

FIELD OF THE INVENTION

The present invention is directed to apparatus and methods for minimizing the risk of air embolism when performing a procedure in a patient's thoracic cavity. A specific application of the invention is described in conjunction with devices and methods for repairing and replacing a mitral valve in a patient's heart, however, the invention may be used in conjunction with any other procedure including repair or replacement of mitral, aortic and other heart valves, repair of septal defects, pulmonary thrombectomy, electrophysiological mapping and ablation, coronary artery bypass grafting, angioplasty, atherectomy, treatment of aneurysms, myocardial drilling and revascularization, as well as neurovascular and neurosurgical procedures.

BACKGROUND OF THE INVENTION

Various types of surgical procedures are currently performed to investigate, diagnose, and treat cardiovascular diseases. Using current techniques, many of these procedures require a gross thoracotomy, usually in the form of a median sternotomy, to gain access to the patient's thoracic cavity. A saw is used to cut the sternum longitudinally thereby allowing two opposing halves of the anterior or ventral portion of the rib cage to be spread apart. A large opening in the thoracic cavity is created through which the surgical team may directly visualize and operate upon the heart and other thoracic contents.

Surgical intervention in the heart generally requires isolation of the heart and coronary blood vessels from the remainder of the arterial system and arrest of cardiac function. The heart is usually isolated from the arterial system by introducing an external aortic cross-clamp through a sternotomy and applying the clamp to the aorta between the brachiocephalic artery and the coronary ostia. Cardioplegic fluid is then injected into the coronary arteries, either directly into the coronary ostia or through a puncture in the aortic root, to arrest cardiac function. In some cases, cardioplegic fluid is injected into the coronary sinus for retrograde perfusion of the myocardium. The patient is then placed on cardiopulmonary bypass to maintain peripheral circulation of oxygenated blood.

Another method of arresting the patient's heart is disclosed in U.S. Pat. No. 5,433,700, which is assigned to the assignee of the present application and is herein incorporated by reference. U.S. Pat. No. 5,433,700 describes an endovascular catheter system for establishing arrest of cardiac function. The endovascular catheter system does not require a gross thoracotomy and facilitates less invasive methods of performing cardiopulmonary procedures.

Once the patient is placed on cardiopulmonary bypass, various surgical techniques may be used to repair a diseased or damaged valve, including annuloplasty (contracting the valve annulus), quadrangular resection (narrowing the valve leaflets), commissurotomy (cutting the valve commissures to separate the valve leaflets), shortening mitral or tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the natural valve and securing a replacement valve in the valve position usually by suturing the replacement valve to the natural valve annulus. Various types of replacement valves are in current use, including mechanical and biological prostheses, homografts, and allografts, as described in Bodnar and Frater, *Replacement Cardiac Valves* 1–357 (1991), which is incorporated herein by reference. A comprehensive discussion of heart valve diseases and the surgical treatment thereof is found in Kirklin and Barratt-Boyes, *Cardiac Surgery*, pp. 323–459 (1986), the complete disclosure of which is incorporated herein by reference.

The mitral valve, located between the left atrium and left ventricle of the heart, is most easily reached through the wall of the left atrium, which normally resides on the posterior side of the heart, opposite the side of the heart that is exposed by a median sternotomy. Therefore, in order to access the mitral valve via a sternotomy, the heart is rotated to bring the left atrium into an anterior position accessible through the sternotomy. An opening, or atriotomy, is then made in the right side of the left atrium, anterior to the right pulmonary veins. The atriotomy is retracted by means of sutures or a retraction device, exposing the mitral valve directly posterior to the atriotomy. One of the aforementioned techniques may then be used to repair or replace the valve.

An alternative technique for mitral valve access may be used when a median sternotomy and/or rotational manipulation of the heart are undesirable. In this technique, a large incision is made in the right lateral side of the chest, usually in the region of the fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for manipulation of surgical instruments, removal of excised tissue, and/or introduction of a replacement valve through the atriotomy for attachment within the heart. However, these invasive, open-chest procedures produce a high degree of trauma, a significant risk of complications, an extended hospital stay, and a painful recovery period for the patient. Moreover, while heart valve surgery produces beneficial results for many patients, numerous others who might benefit from such surgery are unable or unwilling to undergo the trauma and risks of current techniques.

A problem which occurs in conventional open-heart procedures is that air enters the heart during the procedure and must be removed from the heart after completing the procedure. Air which remains in the circulatory system after the heart is closed may produce air emboli which could travel to the brain and cause a stroke or death. Conventional de-airing techniques include mechanical manipulations and venting of the heart to remove air trapped in the heart. U.S. Pat. No.

5,370,631, for example, discloses an apparatus for de-airing the heart which includes a slotted-needle and a resilient bulb.

Carbon dioxide has been used to displace air in the patient's thoracic cavity to help prevent air emboli. In animal studies, carbon dioxide has been shown to be as much as twelve times more soluble in blood than air. Thus, displacing air with carbon dioxide may be beneficial in reducing the harmful effects of gas emboli.

In open-heart procedures, carbon dioxide has been introduced into the thoracic cavity through the median sternotomy. Since the patient's chest is open, the carbon dioxide in the chest cavity readily disperses out of the chest and, therefore, carbon dioxide must be continuously or periodically replaced, Ng and Rosen, "Carbon Dioxide in the prevention of air embolism during open-heart surgery", Thorax 23:194–196 (1968).

Thus, a problem with previous use of carbon dioxide in open heart procedures is that air is free to enter the open chest cavity and high carbon dioxide concentrations cannot be maintained in the chest cavity for extended periods of time without requiring continuous or periodic injection of carbon dioxide.

SUMMARY OF THE INVENTION

In accordance with the principles of the present invention, methods and apparatus for reducing the risk of air embolism when performing a procedure in a patient's thoracic cavity are provided. In an aspect of the present invention an instrument delivery member is inserted into a patient's thoracic cavity between adjacent ribs thereby forming a percutaneous intercostal penetration. The instrument delivery member has a gas outlet for injecting a gas, preferably carbon dioxide, into the patient's thoracic cavity. The gas displaces air from the patient's thoracic cavity thereby reducing the risk of air emboli. The instrument delivery member also has a throughhole sized to permit an instrument to pass therethrough.

The present invention is particularly useful when performing the mitral valve replacement and repair procedures described in U.S. patent application Ser. No. 08/485,600 now abandoned and U.S. patent application Ser. No. 08/163,241 now U.S. Pat. No. 5,571,215 both of which are assigned to the assignee of the present application and which are incorporated herein by reference. The methods facilitate surgical intervention within the heart or great vessels without the need for a gross thoracotomy. The procedure is carried out through small incisions within intercostal spaces of the rib cage without cutting, removing, or significantly deflecting the patient's ribs or sternum thereby reducing the trauma, risks, recovery time and pain that accompany conventional techniques. The devices and methods permit removal of tissue from the thoracic cavity and introduction of surgical instruments, replacement valves and the like into the thoracic cavity, to facilitate heart valve repair and replacement. The devices and methods facilitate replacement of a heart valve with various types of prostheses, including mechanical and biological prostheses, homografts, and allografts.

In a preferred embodiment of the present invention, the instrument delivery member includes a plurality of gas outlets which are angled toward the distal end to help retain gas in the patient's thoracic cavity. In an alternative embodiment, the gas outlets are angled substantially perpendicular to the longitudinal axis of the instrument delivery member with the gas passing adjacent the distal end. A vacuum pump may also be provided for withdrawing air from the patient's thoracic cavity or for capturing gas escaping from the patient's thoracic cavity.

The concentration of gas in the patient's thoracic cavity is preferably monitored so that a threshold gas concentration is maintained. When using carbon dioxide, the gas concentration is preferably at least 70% and more preferably at least 90% by volume. Alternatively, the air concentration may be maintained at no more than 50% and more preferably no more than 5% by volume. The humidity and temperature in the patient's thoracic cavity are also preferably monitored to maintain a desirable humidity and temperature. The relative humidity in the patient's thoracic cavity is preferably at least 10% and more preferably at least 50%. The temperature of the gas is also preferably maintained at a temperature below body temperature and preferably below 20 (degrees) C.

The pressure of the gas in the patient's thoracic cavity is also preferably monitored and regulated. The gas pressure is preferably maintained at a pressure higher than the pressure outside the thoracic cavity to prevent air does from entering the thoracic cavity. When performing the procedure described in U.S. patent application Ser. No. 08/485,600 now abandon, which is incorporated herein by reference, a number of instrument delivery members, such as cannulas or trocars, are inserted into the patient to perform a mitral valve procedure. The present invention provides seals at the instrument delivery members to prevent the escape of gas so that the pressure can be maintained in the thoracic cavity. Such seals are commonly used in laparoscopic procedures. Unlike laparoscopic surgery, however, the pressure in the thoracic cavity is not used to retract the thoracic cavity and, as such, the pressure in the thoracic cavity is kept between 1 and 14 mm Hg and more preferably between 1 and 10 mm Hg and most preferably between 1 and 8 mm Hg all of which are below the pressures used in laparoscopic procedures which are typically between 15 and 20 mm Hg.

In another aspect of the present invention, the instrument delivery member includes a gas inlet and a gas outlet positioned to receive gas issuing from the gas inlet. The gas passing from the gas inlet to the gas outlet preferably passes across the throughhole, and preferably transects the throughhole, to act as a gas shield which minimizes gas losses through the instrument delivery member. The gas shield advantageously permits the introduction of instruments through the instrument delivery member without significantly hindering use of instruments. The gas which is used for the gas shield may be any gas such as carbon dioxide or air. A blower, fan or compressor is coupled to the gas inlet and may also be coupled to the gas outlet for closed circuit circulation.

In yet another aspect of the invention, a vent is provided for venting gas from the left ventricle when performing a procedure on the patient's heart such as a mitral valve repair or replacement. The vent includes first and second lumens and first and second outlets fluidly coupled to the first and second lumens, respectively. The first lumen and first outlet are used for injecting gas into the patient's heart and for evacuating gas from the heart when the heart is being closed after the mitral valve replacement or repair procedure. The second lumen and second outlet are used for sampling gas in the patient's thoracic cavity.

In a specific application of the vent, the vent is positioned in the left ventricle and a gas, such as carbon dioxide, is injected into the patient through the first lumen. The gas displaces air in the left ventricle so that when the heart is closed the presence of air is minimized to minimize the risk of air emboli. The gas is preferably injected into the heart using the temperature, pressure, humidity and gas concentration monitoring and control system described above. When the heart is closed, the first lumen and first outlet are used to evacuate gasses from the heart. The second outlet and second lumen are used to collect gasses in the thoracic cavity for measuring pressure, temperature, humidity, and/or gas concentrations. The second outlet is spaced apart from the distal end so that the measurements are not overly influenced by the gas being injected into the left ventricle through the first lumen and first outlet.

In yet another aspect of the invention, an enclosure is provided around the patient for providing a sealed operating space. A gas, such as carbon dioxide, is maintained in the sealed operating space so that air does not enter the patient's cardiopulmonary system during a medical procedure. The enclosure includes a seal, such as a drape, which engages the patient and provides a substantially air tight seal. The enclosure includes arm pass-throughs which are used by the surgeon to perform the medical procedure in the enclosure. An advantage of the enclosure is that it may also be used in conventional open heart procedures since a gas environment is created around the patient.

The terms "percutaneous intercostal penetration" and "intercostal penetration" as used herein refer to a penetration, in the form of a small cut, incision, hole, or the like through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. It is understood that one or more ribs may be retracted or deflected a small amount and/or a small amount of intercostal cartilage may be removed without departing from the scope of the invention.

These and other advantages of the invention will become apparent from the following detailed description of the invention.

BRIEF DESCRIPTION OF THE DRAWINGS

FIG. 3 is an isometric view of the instrument delivery member having a gas delivery assembly;

FIG. 4. is an isometric view of the gas delivery assembly of FIG. 3;

FIG. 9 is a plan view of the vent of FIG. 8;

FIG. 9A is a side view of an alternate embodiment of the left ventricle vent of FIG. 9;

FIG. 10 is a side view of the vent of FIG. 8;

FIG. 11 is a cross-sectional view of the vent of FIG. 8 showing first and second lumens;

DETAILED DESCRIPTION OF THE PREFERRED EMBODIMENTS OF THE INVENTION

Figure 1:
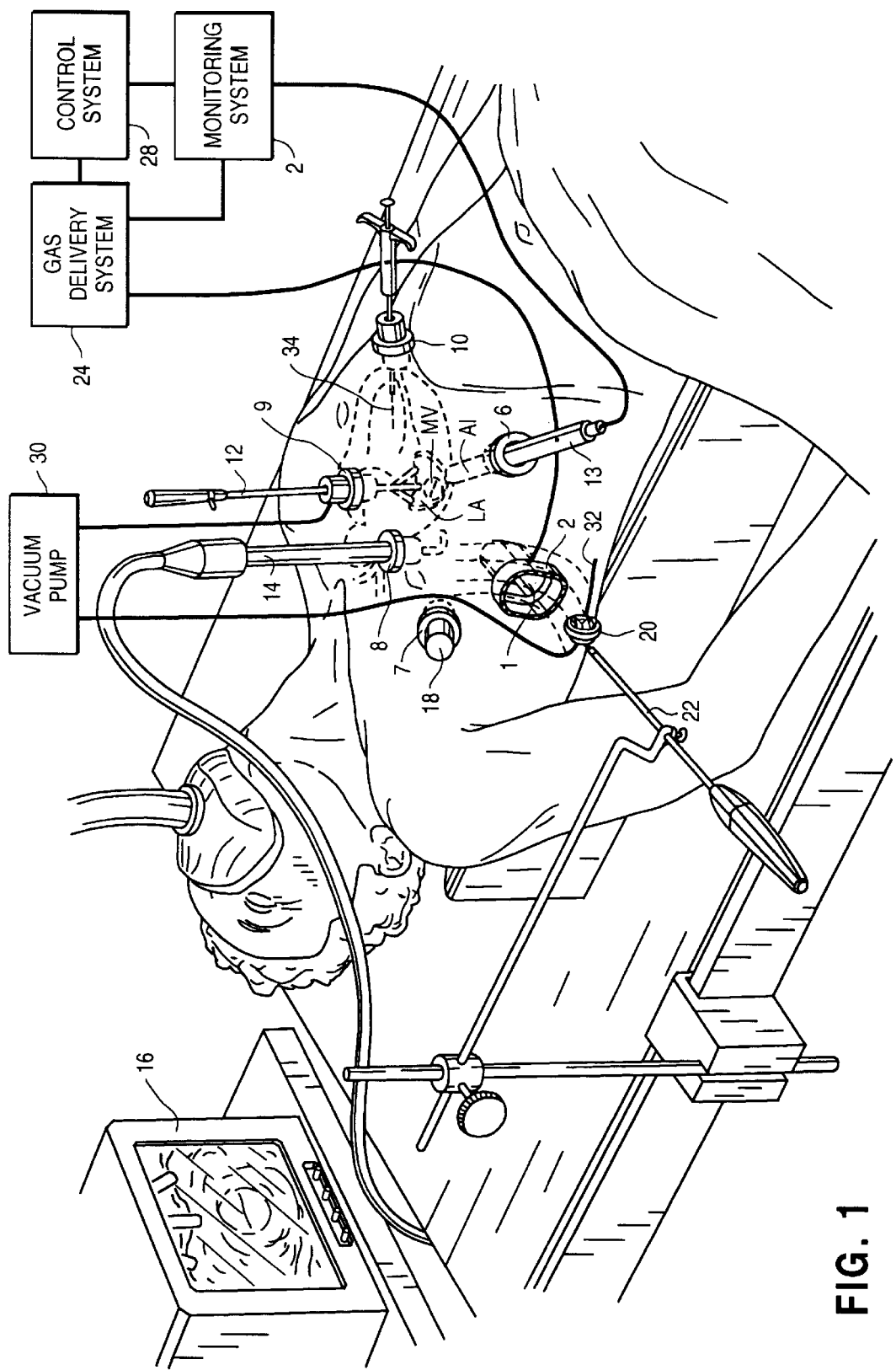
FIG. 1. shows a patient prepared for a mitral valve replacement with a number of instrument delivery members extending into the patient's thoracic cavity and a gas delivery system coupled to one of the instrument delivery members.

Referring to FIG. 1, a system for minimizing the risk of air emboli when performing a procedure in a patient's thoracic cavity is shown. A specific application of the invention is developed herein with respect to a minimally invasive mitral valve replacement procedure, however, the apparatus and methods of the present invention may be used in conjunction with any other procedure including repair or replacement of aortic and other heart valves, repair of septal defects, pulmonary thrombectomy, electrophysiological mapping and ablation, coronary artery bypass grafting, angioplasty, a therectomy, treatment of aneurysms, myocardial drilling and revascularization, as well as neurovascular and neurosurgical procedures. The procedure for performing the minimally invasive mitral valve repair and replacement will be discussed to the extent necessary to adequately describe the present invention and a complete discussion is provided in U.S. patent application Ser. No. 08/485,600 now abandoned, filed Jun. 7, 1995, which is incorporated herein by reference.

Referring still to FIG. 1, an instrument delivery member 2 includes a throughhole 4 for introduction of surgical instruments into a patient's thoracic cavity. The instrument delivery member 2 is preferably a hollow tube, such as a cannula, trocar sleeve, a 3-sided channel-shaped member, a ring retractor, a wound retractor having a pair of adjustable parallel blades, or any other device which facilitates introduction of a medical instrument into a patient between adjacent ribs. The instrument delivery member 2 is positioned between adjacent ribs in the patient and a number of other instrument delivery members 6–10 are positioned at various other positions thereby forming a number of percutaneous intercostal penetrations.

A retractor 12 passes through instrument delivery member 9 and various sensors 13, which are described in greater detail below, pass through instrument 10 delivery member 6. A thoracoscope 14 passes through instrument delivery member 8 and is coupled to a monitor 16 for viewing the patient's thoracic cavity. Any other viewing device may be used in conjunction with, or as a substitute for, the thoracoscope 14. A first removable plug 18 is positioned in the delivery member 7 with the first plug 18 separated from the instrument delivery member 7 for clarity. A replacement valve 20 is mounted to a holder 22, however, a repair device, such as a ring for annuloplasty, may, of course, be used when repairing rather than replacing the mitral valve.

A gas delivery system 24 is coupled to the instrument delivery member 2 for delivering a gas into the patient's thoracic cavity. The gas delivery system 24 supplies gas, such as carbon dioxide, for introduction into the patient's thoracic cavity to minimize the risk of an air embolism when performing a procedure in the patient's thoracic cavity. A monitoring system 26 is coupled to the sensors 13 for monitoring the various conditions sensed by the sensors 13. A control system 28 receives the information from the sensors 13 via the monitoring system 26 and sends control information to the gas delivery system 24 based upon the sensor data. The gas delivery system 24, control system 28 and monitoring system 26 are described in greater detail below in connection with FIG. 16.

A vacuum pump 30 is coupled to the instrument delivery member 9 having the retractor 12 for withdrawing air from the thoracic cavity when the gas is injected into the thoracic cavity. The vacuum pump 30 is also coupled to a line 32 which is positioned adjacent to the instrument delivery member 2 for withdrawing gas which escapes through the instrument delivery member. A vent needle 34 extends through the instrument delivery member 10 and into the patient used for venting gasses from the thoracic cavity as described in further detail below.

Figure 2:
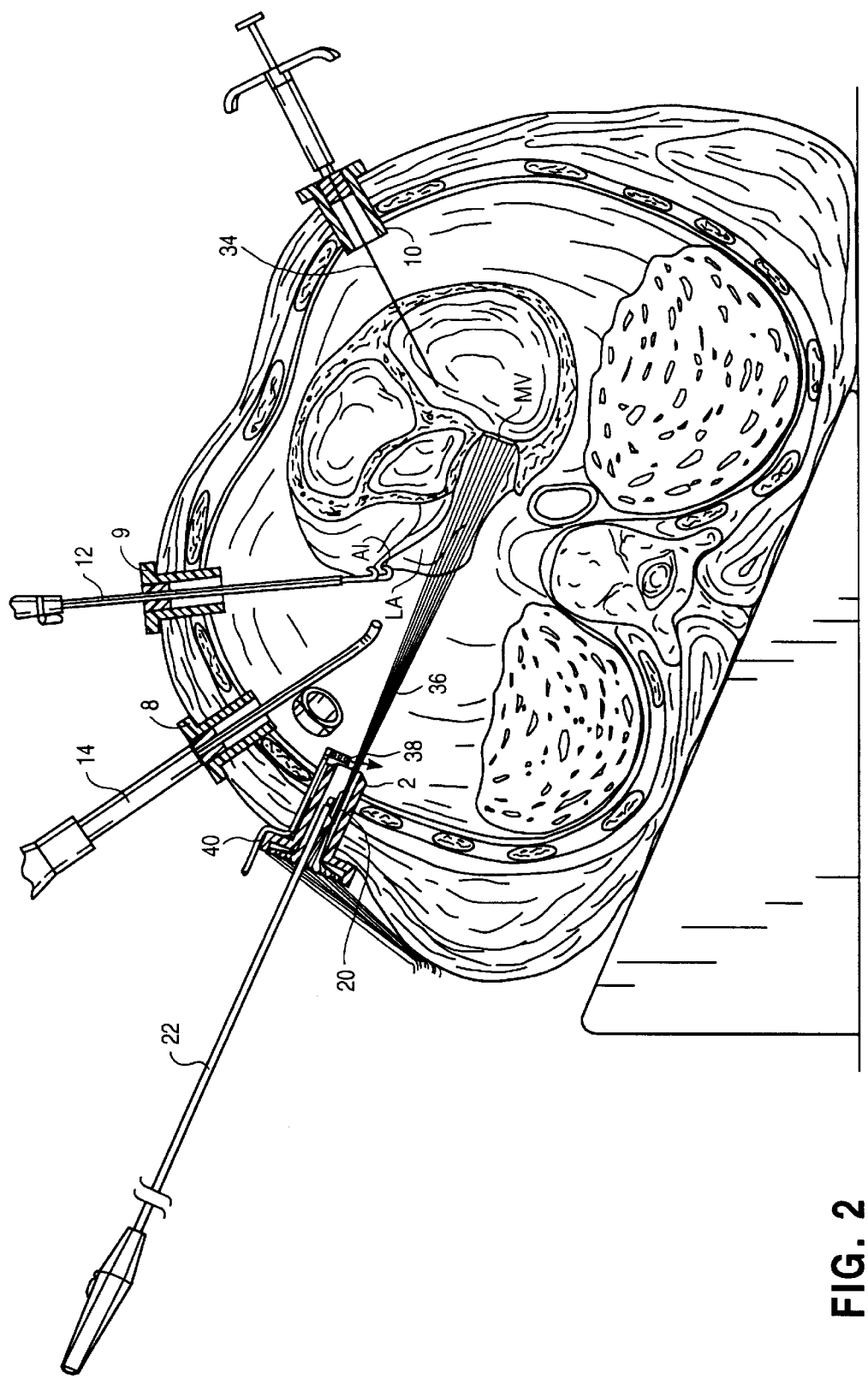
FIG. 2 shows a cross-sectional view of the patient of FIG. 1 with a gas outlet coupled to one of the instrument delivery members for injecting a gas into the patient's thoracic cavity.

Referring to FIG. 2, a cross-sectional view of the patient is shown. The vent needle 34 is preferably perforated along the longitudinal axis (not shown) of the needle for venting gasses from the left ventricle. Use of the vent needle 34 is described in greater detail below in connection with preferred methods of operation. The retractor 12 engages an atriotomy AI formed in the patient's heart for retracting the atriotomy open. A number of sutures 36 extend through the instrument delivery member 2 and are used for attaching the repair valve 20 in the manner described in U.S. patent application Ser. No. 08/485,600 now abandoned.

The instrument delivery member 2 includes a gas outlet 38, preferably a number of gas outlets, and a gas inlet 40 coupled to the gas delivery system 24 for delivering the gas into the thoracic cavity. A gas, such as carbon dioxide, is introduced into the patient's thoracic cavity through the gas outlet 38. Referring to FIGS. 3 and 4, the instrument delivery member 2 and a gas delivery assembly 42 are shown. The instrument delivery member 2 preferably includes a sidewall 44 and the throughhole 4 defines a longitudinal axis 46. The throughhole 4 extends from a proximal end and terminates at an opening 48 at a distal end 50. Although the instrument delivery member 2 preferably has an oval throughhole, any other cross-section may be used such as a race-track, rectangular, trapezoidal, elliptical or circular cross-sectional shape.

The throughhole 4 is preferably sized to allow an annuloplasty ring or replacement valve mounted on a holder to pass therethrough. The throughhole 4 preferably has a cross-sectional shape having a width of preferably about 10–30 mm, and more preferably 15–25 mm, and a height of preferably about 25–75 mm, more preferably 30–50 mm. Furthermore, the width or height of the throughhole is preferably at least 2 cm, more preferably at least 2.5 cm and most preferably at least 3 cm. Typical laparoscopic trocars have much smaller openings since gas losses must be minimized when operating at the higher pressures used in laparoscopic procedures. The exact width and height will often be determined by the width (or diameter) and height of the annuloplasty ring or replacement valve and holder being used in the procedure. It is sometimes desirable to begin the procedure with a instrument delivery member 2 of the minimum size necessary to assess the condition of the native valve. For example, an instrument delivery member 2 having a width of about 15–20 mm may be used initially. When the size of the annuloplasty ring or prosthetic valve has been selected, the smaller instrument delivery member may be replaced, if necessary, with a larger instrument delivery member to accommodate the prosthesis.

The instrument delivery member 2 is configured for placement in an intercostal space preferably without retraction of ribs, or at least minimal retraction of ribs, and preferably has an external width of less than about 30 mm, and preferably less than about 25 mm. Although it is preferred to provide a sidewall 44 which has an elongate tubular structure with a length sufficient to extend into the thoracic cavity, the sidewall may simply be the elements of a ring retractor or any of the other instrument delivery members described above so long as the instrument delivery member provides access to the patient's thoracic cavity for surgical instruments. The instrument delivery member has a flange 52 at its proximal end which engages the outside of the patient's chest. The instrument delivery member 2 has a length sufficient to extend from outside of the chest, through the intercostal space, and into the chest cavity just beyond the interior of the chest wall. The instrument delivery member 2 preferably has a length of about 20–70 mm and more preferably about 30–50 mm from the flange 52 to the distal end.

The instrument delivery member 2 includes a suture organizing ring 54 attached to the flange 52. Organizing ring 54 has a plurality of circumferentially-spaced radial slots 56 or suture holders in which a suture thread may be received and retained. Slots 56 have tapered upper ends 58 for guiding a suture thread to the slot. Suture organizing ring 54 allows sutures placed in the heart for attachment of a prosthesis to be drawn through the throughhole and temporarily placed in slots 56 to keep the sutures individually separated and untangled. In order to facilitate introducing instrument delivery member 2 through a puncture or small incision between the ribs, an obturator (not shown) may be inserted into the throughhole 4. The instrument delivery member 2 may also be made of a flexible or deformable material to allow it to be shaped by the user or to conform to the shape of the intercostal space.

Still referring to FIGS. 3 and 4, the gas delivery assembly includes a sleeve 60 which clips onto the sidewall 44. The sidewall 44 may include ribs (not shown) for enhanced engagement with the gas delivery assembly 42. The gas outlet 38, and preferably a plurality of gas outlets, are provided on a horseshoe shaped ring 61. The gas delivery assembly 42 is mounted to the sidewall 44 so that a plurality of gas outlets 38 are directed across the opening 48. In the preferred embodiment, the opening 48 lies in a plane perpendicular to the longitudinal axis 46 so that the gas outlets 38 are also directed substantially perpendicular to the longitudinal axis. The opening 48 may also be skewed with respect to the longitudinal axis with the gas outlets 38 also being skewed so that the gas outlets 38 are configured to issue gas directly across the opening 48. By orienting the gas outlets 38 in this manner, the gas injected into the patient helps retain the gas in the thoracic cavity by creating a gas curtain at the opening 48 of the instrument delivery member. Although it is preferred to provide one gas delivery assembly, two or more gas delivery assemblies may be provided. Furthermore, although it is preferred to direct the gas in a direction perpendicular to the longitudinal axis 46, the gas outlets 38 may also be angled toward the distal end or, alternatively, angled toward the proximal end with a baffle to redirect the gas so that the gas does not simply exit through the proximal opening in the instrument delivery member 2. Finally, the gas outlets 38 are preferably positioned so that they direct gas across substantially the entire width or height of the throughhole 4 so that gas losses through the throughhole are minimized.

A plug 62 is removably mounted to the instrument delivery member 2 to close, or at least partially close, the throughhole 4 thereby minimizing gas losses through the throughhole 4. The second plug 62 preferably includes a resilient surface 63, preferably an elastic band, which engages the instrument delivery member 2 to provide a snug fit when sutures are positioned through the throughhole 4. The second plug 62 has an opening 64 so that instruments may still be passed through the throughhole while reducing losses through the throughhole. A third plug 66 closes the opening 64 so that substantially all gas losses through the throughhole 4 are eliminated. Alternatively, a number of different plugs having different sized openings, or no openings at all like second plug 62A, may be provided. Furthermore, the opening 64 may be any other shape such as H-shaped, an oval ring, Z-shaped or a figure "8."

Figure 5:
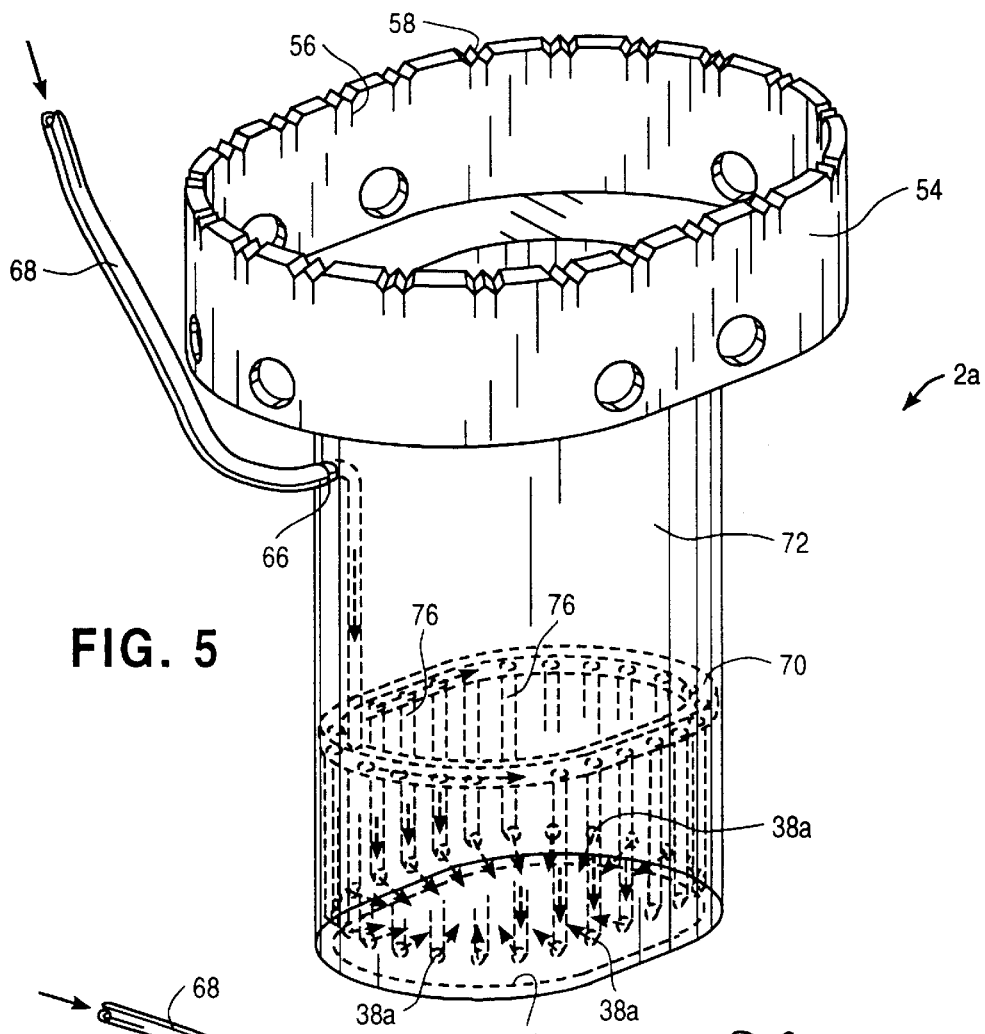
FIG. 5 is a cross-sectional view of a second preferred embodiment of the instrument delivery member.
Figure 6:
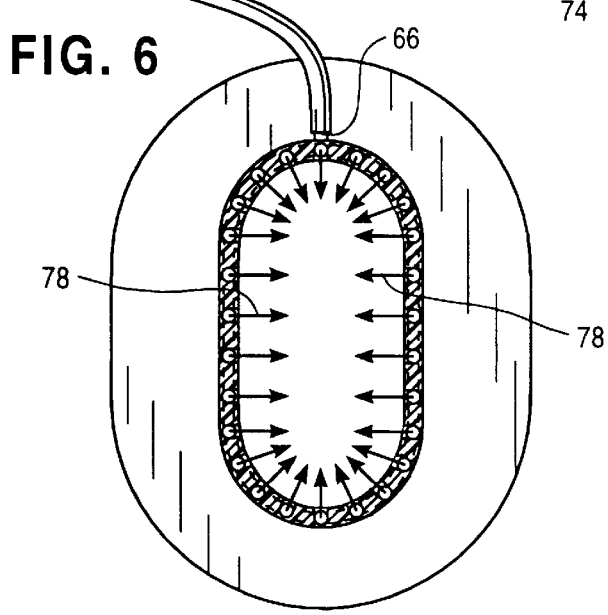
FIG. 6 is an end view of the instrument delivery member of FIG. 5.
Figure 7:
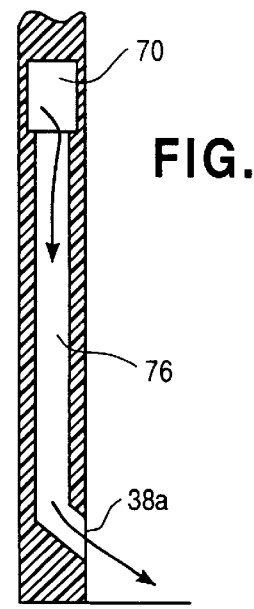
FIG. 7 is a cross-sectional view of a gas path showing the orientation of a gas outlet of the instrument delivery member of FIG. 5.

Referring to FIGS. 5–7, another instrument delivery member 2A is shown which includes integrally formed gas outlets 38A wherein similar reference numbers are used to represent similar features described in the embodiment of FIGS. 3–4. The discussion above concerning instrument delivery member 2 is equally applicable here and the preferred features for the instrument delivery member 2 are also preferred with the instrument delivery member 2A.

The instrument delivery member 2A includes a gas inlet 66 configured to be coupled to a gas line 68 which, in turn, is coupled to the gas delivery system 24.

The instrument delivery member 2A includes integrally formed gas outlets 38A whereas the instrument delivery member 2 includes the removable gas delivery assembly 42. The gas inlet 66 is coupled to a chamber 70 which extends circumferentially around the instrument delivery member 2A between an inner wall 72 and an outer wall 74. A plurality of gas channels 74 extend from the common chamber 70 and 76 terminate at the gas outlets 38A which direct the gas in the direction of arrows 78. The gas outlets 38A are preferably directed toward the distal end and, further, are directed toward the middle of the instrument delivery member 2A. The gas outlets 2A cooperate with one another to hinder escape of gasses through the instrument delivery member 2A.

The gas outlets 38A are particularly useful for providing a pressure in the thoracic cavity above the pressure outside the thoracic cavity to help keep air out of the thoracic cavity. Although it is preferred to angle the gas outlet 38A toward the distal end, the gas outlet 38A may be oriented in any other manner so long as the gas outlet 38A tends to prevent gas from escaping through the open proximal end of the instrument delivery member 2A. Furthermore, although it is preferred to provide a number of gas outlets 38A around the entire periphery of the instrument delivery member 2A, the gas outlets 38A may also be provided only along a section of the instrument delivery member 2A.

Figure 8:
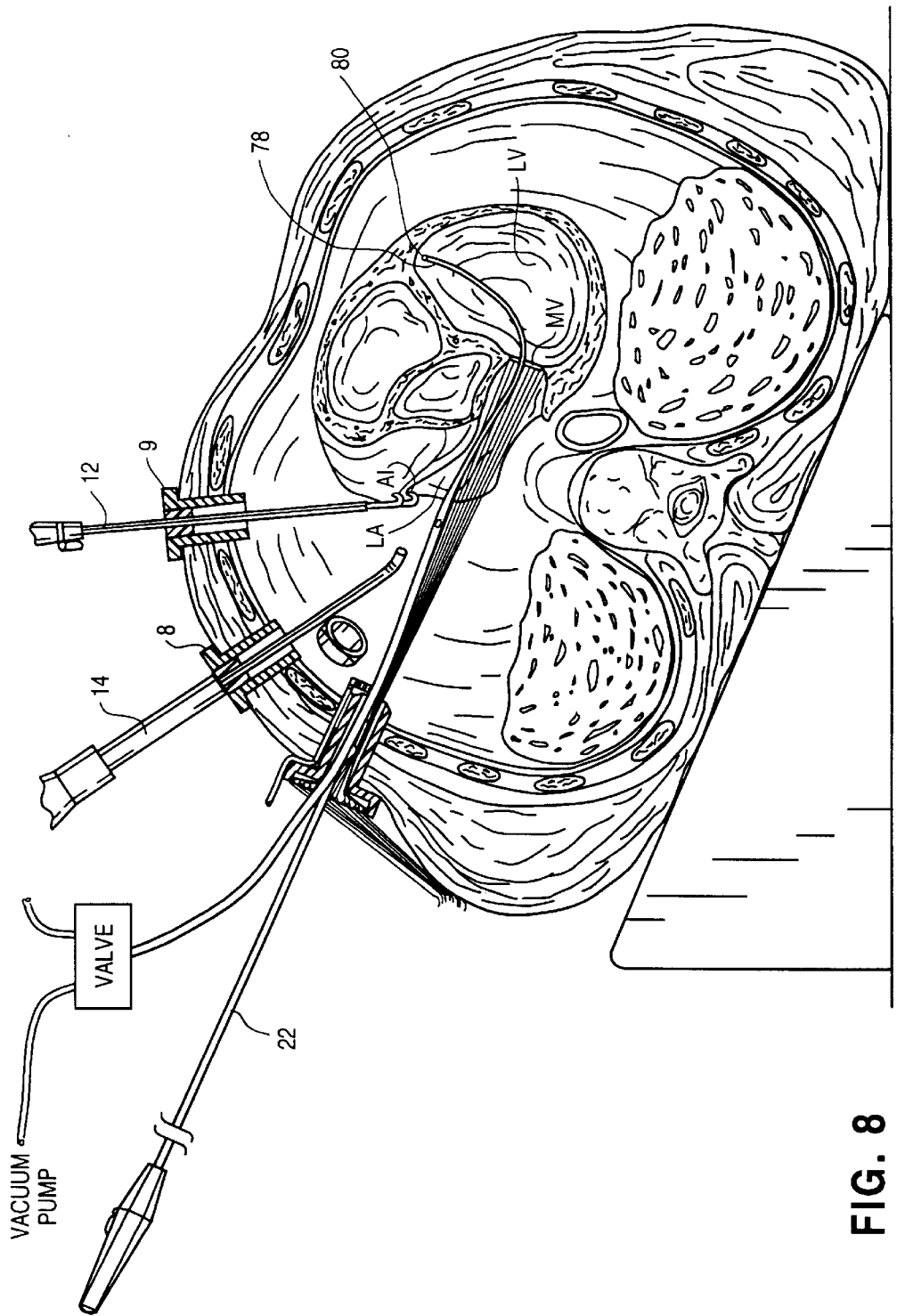
FIG. 8 is a cross-sectional view of a patient with a vent extending through the instrument delivery member and into the patient's left ventricle.

Referring to FIG. 8, a cross-sectional view of the patient is shown with a vent 78 extending into the left ventricle LV. The vent 78 preferably has a distal end 80 which extends to the apex of the left ventricle LV for venting the left ventricle LV. The distal end 80 preferably includes a soft tip for preventing trauma to the left ventricle. The first outlet 86 is preferably used for injecting gas into the left ventricle and for venting gas from the left ventricle. The second outlet is preferably coupled to a monitoring system 26 for monitoring the conditions in the patient's thoracic cavity such as the gas concentration, humidity, temperature and pressure. Use of the vent 78 is described below in connection with discussion of preferred methods of present invention.

Referring to FIGS. 9–11, a distal portion 81 of the vent 78 is shown in a natural, unbiased shape. The distal portion 81 of the vent 78 is configured to position the distal end 80 at the apex of the left ventricle LV when the proximal portion extends through the valve annulus. The approximate position of the valve annulus is shown at broken line 79 which also indicates the beginning of the distal portion 81. The vent 78 preferably includes a first lumen 82, a second lumen 84 and first and second outlets 86, 88 fluidly coupled to the first and second lumens 26, respectively. The first and second outlets 86, 88 are preferably spaced apart between 0.5 and 8 cm, and more preferably between 2 and 4 cm, so that gas samples taken through the first outlet are not overly influenced by gas injected into the left ventricle through the first outlet 88. The first outlet 86 is preferably positioned near the distal end 80 and the second outlet 88 is preferably between at least 0.5, more preferably at least 5 cm and most preferably at least 8 cm from the distal end. The distal portion 81 preferably extends between 1 and 10 cm, and more preferably between 1 and 5 cm in the axial direction A, and extends in the radial direction B between 0 and 15 cm and more preferably 2 and 8 cm, and extends between 0 and 5 cm and more preferably between 0.5 and 3 cm in the other radial direction C. The proximal end of the vent 78 is flexible so that the user may position the vent 78 where it will not interfere with the medical procedure. Referring to FIG. 9A, the distal end of another left ventricle vent 78A is shown. The left ventricle vent 78A has the same preferred dimensions as the left ventricle vent 78, however, the first and second outlets 86A, 88A are both positioned near the proximal end with an angle D therebetween. The angle D is preferably at least 90 degrees and preferably greater than 90 degrees so that gas issuing from the first outlet 86A does not overly influence gas samples taken at second outlet 88A.

Figure 12:
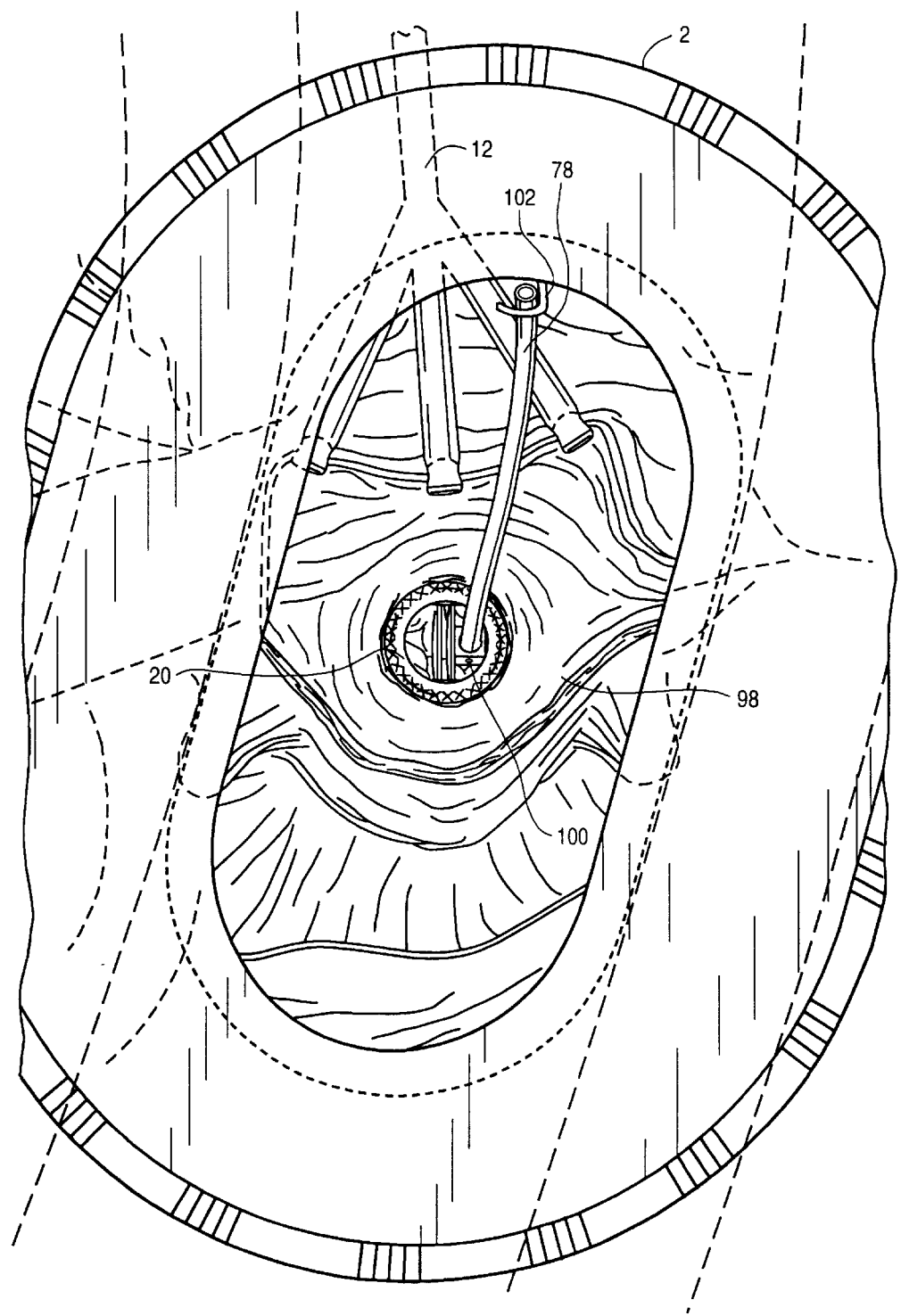
FIG. 12 is a view looking through the instrument delivery member with a mitral valve being attached to the patient's valve annulus.

Referring to FIGS. 12, a view through the throughhole 4 of the instrument delivery member 2 is shown. A spacer 98 prevents contact between the valve 20, which in this case is a mechanical valve, and the vent 78. The spacer 98 preferably includes a pair of holes 100 for removing the spacer 98 before closing the heart. Alternatively, the spacer 98 may be dispensed with and the vent 78 may be coated with a lubricious coating of silicone, teflon or polyurethane to prevent damage to the valve 20 when the vent 78 is withdrawn. The instrument delivery member 2 includes a clip 102 for holding the vent 78 after the vent 78 is positioned in the left ventricle LV. The clip 102 prevents movement of the vent 78 and also positions the vent 78 away from the center of the throughhole 4 so that other instruments may be used through the instrument delivery member 2.

Figure 13:
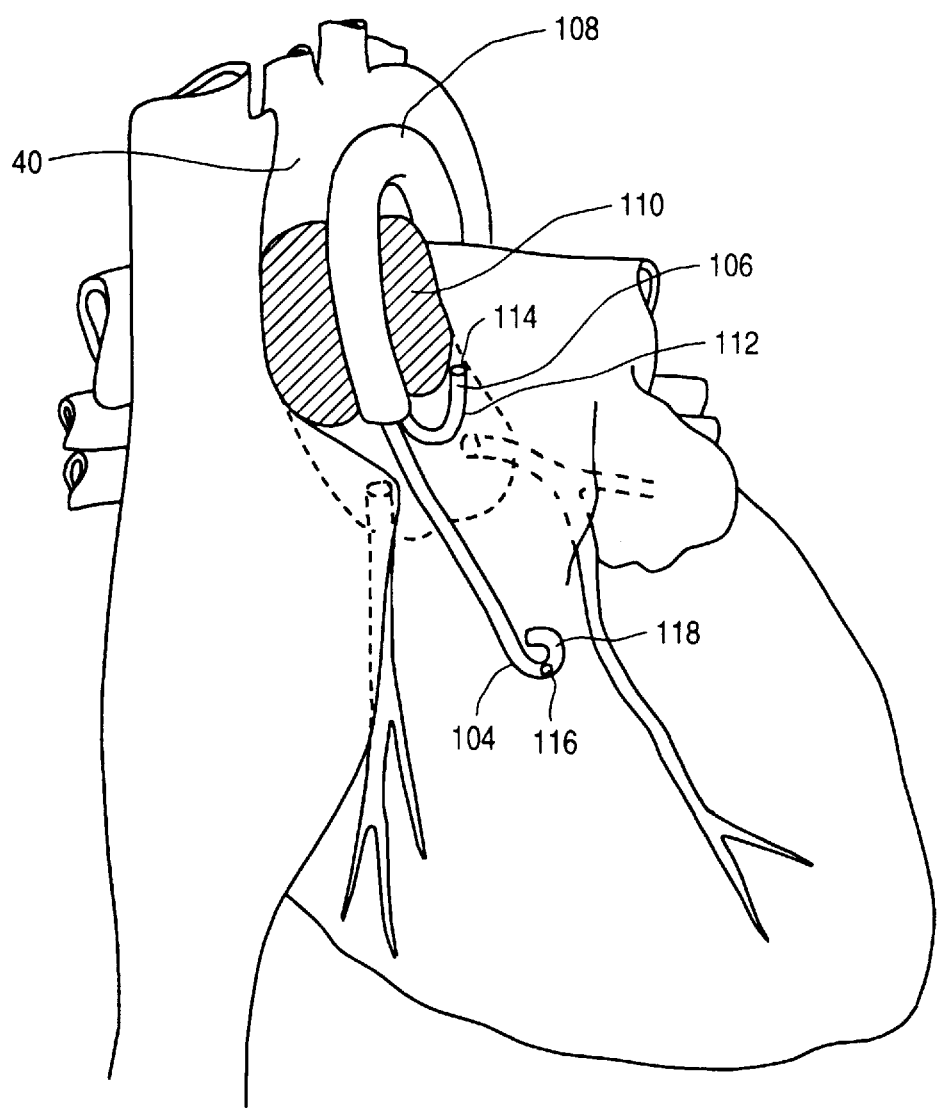
FIG. 13 shows vent catheters extending through a lumen of an endoaortic partitioning catheter.

Referring to FIG. 13, a left ventricle vent 104 and an aortic vent 106 are shown extending through an endoaortic partitioning catheter 108 which is described in U.S. patent application Ser. No. 08/415,366 to Stevens et al. now abandoned which is assigned to the assignee of the present invention and which is incorporated herein by reference. The endoaortic partitioning catheter 108 has an occluding member 110 which occludes the ascending aorta. Cardioplegic fluid is introduced to the coronary arteries through the endoaortic partitioning catheter 110 for arresting cardiac function. The endoaortic partitioning catheter 110 provides a working lumen (not shown) through which instruments, such as the left ventricle vent 104 and aortic vent 106, may pass.

The aortic vent 106 has a curved distal end 112 which generally conforms to the shape of the occluding member 110 for venting gasses around the occluding member 110. The aortic vent 106 has an opening 114 at the distal end 112 for venting gasses from the ascending aorta AO. The proximal end of the aortic vent 106 is relatively stiff so that the aortic vent 106 may be rotated from the proximal end. Rotation of the aortic vent causes the distal end 112 to circumscribe the outer surface of the occluding member 110 for venting gasses around the occluding member 110. When using the aortic vent 106, the patient is preferably tilted feet downward so that gasses in the ascending aorta rise toward the occluding member 110 for venting.

The left ventricle vent 104 has an opening 116 near a curved, distal end 118 for venting the left ventricle. The curved end 118 prevents damage to the aortic valve and the left ventricle when the left ventricle vent 104 passes through the aortic valve and the left ventricle. The curved distal end 118 is preferably curved in an arc greater than 180° so that the curved portion also contacts the aortic valve when the catheter is withdrawn. Use of the aortic vent 106 and left ventricle vent 104 is described below in connection with preferred methods of the present invention. Both the aortic vent 106 are and the left ventricle vent 104 are preferably coupled to the vacuum pump 30 for withdrawing gasses from the patient's heart.

Figure 14:
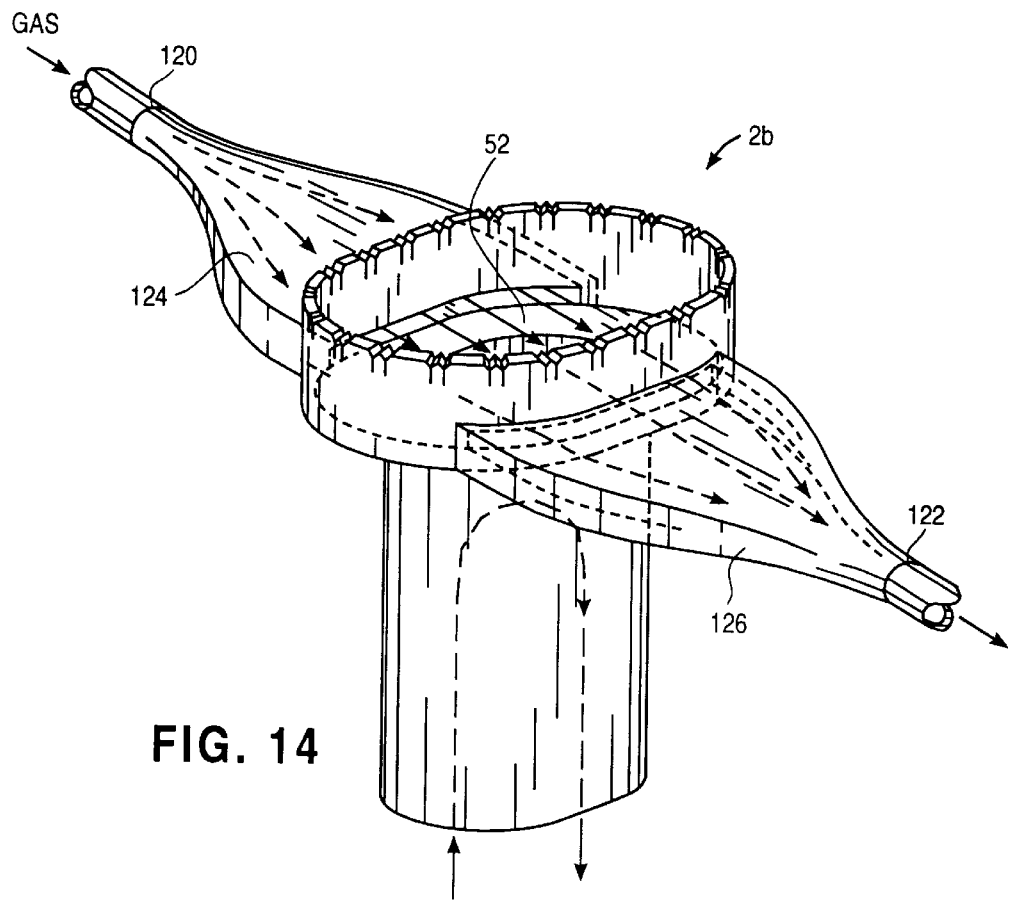
FIG. 14 is an isometric view of another preferred instrument delivery member having a gas inlet and a gas outlet positioned to receive gas issuing from the gas inlet.
Figure 15:
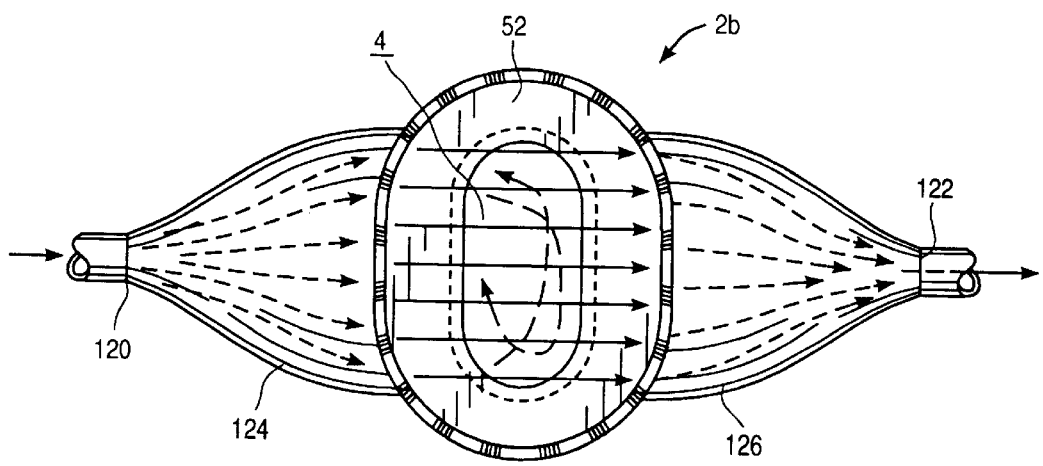
FIG. 15 is a top view of the instrument delivery member of FIG. 14.

Referring to FIGS. 14 and 15, another instrument delivery member 2B is shown which includes both a gas inlet 120 and a gas outlet 122. The instrument delivery member 2B is substantially the same as the instrument delivery members 2 and 2A described above and discussion of the features of the instrument delivery members 2 and 2A are equally applicable here. The gas outlet 122 is positioned to receive gas issuing from the gas inlet 120 so that a gas shield is formed which minimizes escape of gasses from the thoracic cavity. The gas inlet and outlet preferably extend across substantially the entire width and/or length of the throughhole 4 and include tapered entrances 124, 126 so that a laminar flow of gas is achieved. The bottom surfaces of the gas inlet and outlet 120, 122 are preferably flush with the flange 52 so that the flange 52 helps provide the gas shield across the throughhole 4. The gas inlet 120 preferably has a relatively small internal height of between 0.25 and 5 mm and more preferably between 0.5 and 3 mm. The gas outlet 122 may have a somewhat larger internal height of preferably between 1 and 10 mm and more preferably between 2 and 5 mm. The gas outlet 122 is preferably positioned and sized to withdraw substantially all of the gas issuing from the gas inlet 122 so that a gas shield is maintained across the throughhole 4.

The gas inlet and outlet 120, 122 are coupled to a fan, blower or compressor (not shown) for delivering the gas and forming the gas shield with a closed system. A filter (not shown), preferably a hydrophobic filter, filters the gas in the closed system. The gas used for the gas shield may be any gas, such as carbon dioxide or even air, since the gas shield primarily functions to reduce gas losses through the instrument delivery member 2B. The gas shield may be formed with carbon dioxide with the outlet 122 delivering the carbon dioxide into the patient. For example, the instrument delivery member 2B may include the gas delivery assembly 42 with the gas delivery assembly 42 being coupled to the outlet 122. Thus, although the instrument delivery member 2B is an independent device for minimizing gas losses from the patient's thoracic cavity, the gas inlet and gas outlet 120, 122 may also be used in connection with the embodiment of FIGS. 3–4 and 5–7 so that gas is injected into the patient with the same member that is used for forming the gas shield. Although it is preferred to provide the gas inlet 120 at a geometrically opposite side of the instrument delivery member 2B from the gas outlet 122, the instrument delivery member 2B may include baffles and the like so that the gas outlet 122 is not positioned geometrically opposite the gas inlet 120 but, nonetheless, receives the gas issuing from the gas inlet 120. Furthermore, although it is preferred to provide the gas inlet and outlet 120, 122 near the proximal end, the gas inlet and outlet may also be positioned near the distal end of the instrument delivery member 2B similar to orientation of the gas delivery assembly 42.

Figure 16:
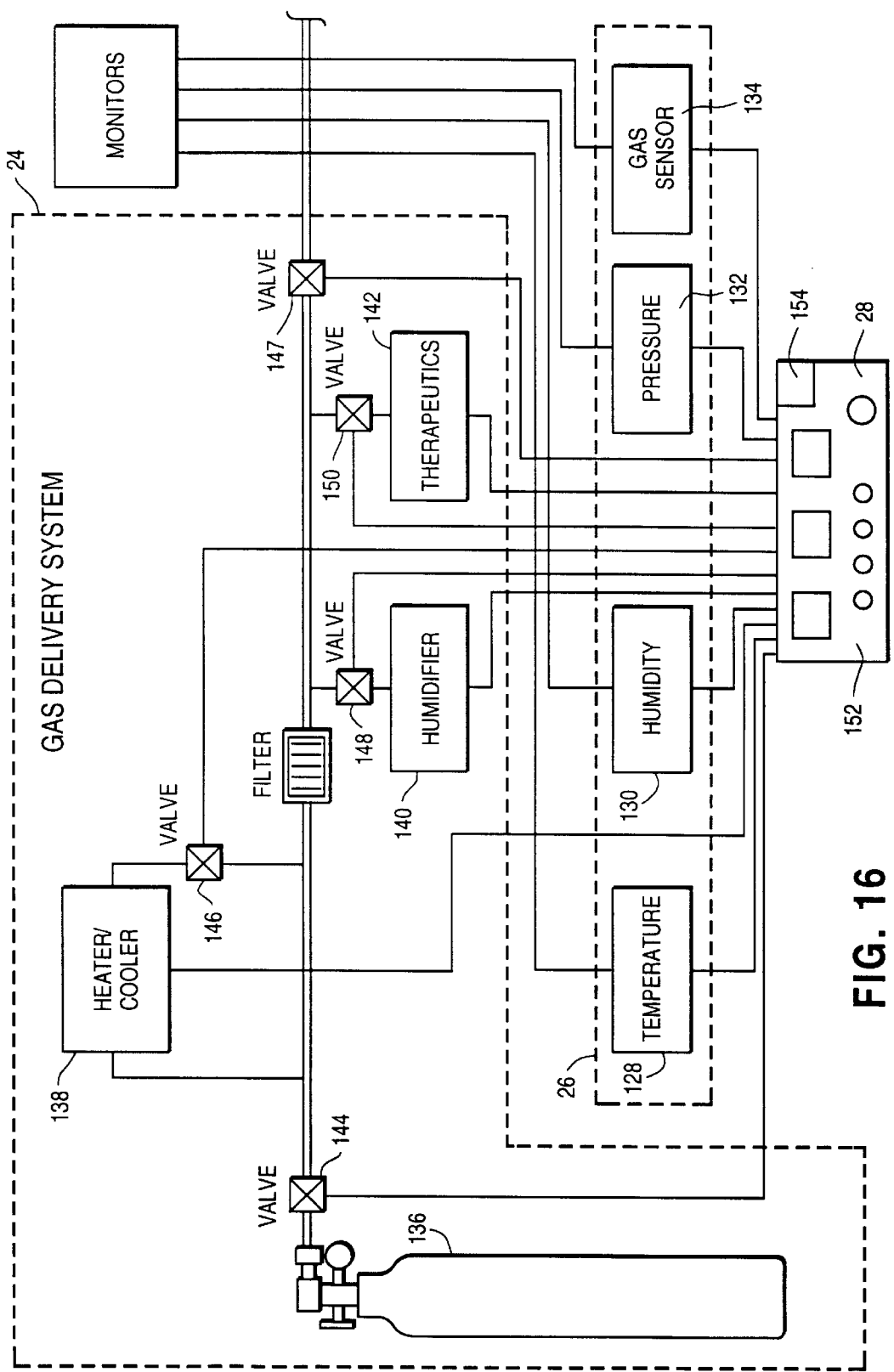
FIG. 16 is a schematic of the gas delivery system, monitoring system and control system.

Referring to FIG. 16, the gas delivery system 24, monitoring system 26 and control system 28 are shown. The monitoring system 26 preferably includes a temperature sensor 128, a humidity sensor 130, a pressure sensor 132 and a gas sensor 134 such as a carbon dioxide or oxygen sensor. Referring to FIG. 1, the sensors 128, 130, 132, 134 extend through the instrument delivery member 6, however, more than one of the instrument delivery member may be used for the sensors 13 if necessary. Alternatively, a sampling tube, such as any of the vents described herein, may be periodically or continuously positioned within the patient for sampling gas which is then delivered to the various sensors outside of the patient. The temperature and humidity sensors 128 are also coupled to the gas delivery line for measuring the temperature and humidity of the gas before injection into the patient's thoracic cavity. The temperature in the patient's thoracic cavity may also be measured and the temperature of the gas injected into the patient may be selected in response to the temperature measured in the patient's thoracic cavity.

The gas delivery system 24 includes a source of gas 136, such as carbon dioxide, a heater and/or cooler 138, a humidifier 140 and a source of therapeutics 142. Although it is preferred to use carbon dioxide any other suitable gas may be used which is absorbed by the body more readily than air so that the risk of harm due to gas emboli is reduced. A discharge valve or regulator 144, which is controlled by the control system 28, controls the flow of gas. The heater/cooler 138 is coupled to the discharge line for heating and/or cooling the gas. A valve 146 regulates the amount of heated or cooled gas added to the gas line from the source of gas 136. It is preferred to cool the gas since lower temperatures are advantageous when performing procedures on the heart and because cooling the gas increases the gas density which may further reduce gas losses from the thoracic cavity. Although it is preferred to provide a separate heating and cooling branch, the entire flow of gas from the source of gas 136 may be passed through the heater/cooler 138 rather than only a portion of the gas stream. Valves 144, 146 and 147 for regulating the gas stream are controlled by the control system 28. The monitoring system 26 may also include a flow rate indicator (not shown) for measuring the flow rate downstream from the valve 147.

The humidifier 140 prevents excessive drying of the patient's tissue during the medical procedure. In a preferred method described below, the thoracic cavity is flooded with gas throughout the procedure which might excessively dry the patient's tissue. In order to prevent excess drying, the humidifier 140 adds water vapor to the gas stream. The humidifier 140 may be any conventional humidifier such as a misting nozzle, a mixing chamber, or an atomizer. The humidifier 140 preferably draws liquid from a source of sterilized saline or water (not shown). A valve 148, which is controlled by the control system 28, regulates the addition of humidified gas to the gas stream in response to the humidity measurements by the humidity sensor 130.

The source of therapeutics adds therapeutic agents, such as antiinflammatories, to the gas stream for, for example, reducing post operative adhesions. A surfactant may also be introduced into the patient's thoracic cavity before filling the heart with blood to reduce the surface tension of bubbles in the heart. A preferred surfactant would be the phospholipid pulmonary surfactant found in the lungs. Reduction of the surface tension facilitates removal of gasses since gas bubbles are less likely to adhere to the heart and other vessels and will pool at locations where the various vents may be used. Other therapeutics which might be delivered include topical anesthetics. The introduction of therapeutics is regulated by a valve 150 which is controlled by the control system 28.

The monitoring system 26 includes the temperature, humidity, pressure and gas concentration sensors 128, 130, 132, 134. Referring to FIG. 1, the sensors 13 have lines which lead to the thoracic cavity which may be electrical wires, when using a pressure transducer for example, or may be sample lines which withdraw gas from the thoracic cavity and are sampled outside the body. A single sample line may branch off to the various sensors or, alternatively, the sensors may be connected together in series. As mentioned above, the left ventricle vent 104 may be coupled to any of the sensors for measuring various parameters in the thoracic cavity. Referring again to FIG. 16, the gas sensor detects the concentration of the gas injected into the thoracic cavity or, alternatively, detects the concentration of air remaining in the thoracic cavity. When using carbon dioxide, the gas concentration sensor 134 is preferably a sensor with the ability to measure 0–100% carbon dioxide concentration in a gas sample at 1–2 atm pressure, 0–37 (degrees) C. and up to 90% relative humidity with a response time of less than about 60 seconds. If necessary for accuracy, the sensor may require that the sample is dried with a dehumidifier (not shown). A number of conventional carbon dioxide sensors may be used which use infra-red sensors, mass spectroscopy, thermal conductivity and electrochemical cell sensors, laser absorption and emission technologies.

The control system 28 receives data from the sensors 13 and is coupled to the various parts of the gas delivery system 24 for controlling the delivery of gas. The control system 28 preferably includes a display 152 for visual indication of the various sensor data such as pressure, temperature, humidity, and gas concentration in the patient's thoracic cavity as well as the gas flow rate into the patient. The control system 28 also preferably includes one or more alarms 154 which indicate when the temperature, humidity, pressure, gas concentration and/or gas flow rate is at an unacceptable level. The alarm 154 may be any conventional alarm such as a visual and/or audible alarm. The control system 28 is preferably adapted to maintain the temperature, humidity, pressure and/or gas concentration at predetermined values. Although it is preferred to provide the entire monitoring system 26, individual pieces of the gas delivery system 24 and monitoring system 26 may be used without departing from the scope of the present invention. Furthermore, although it is preferred to provide a combined system, the various components may, of course, also be provided separately.

Preferred methods of the present invention will now be described in connection with the preferred embodiments. It is understood that the preferred embodiments provide preferred apparatus for performing the methods of the present invention, however, other apparatus may be used without departing from the scope of the invention as defined by the claims. The following preferred methods are described in connection with a mitral valve replacement or repair, however, any of the other procedures mentioned above may also be performed without departing from the scope of the invention. A complete discussion of a preferred method of mitral valve replacement is described in U.S. patent application Ser. No. 08/485,600, filed Jun. 7, 1995 now abandoned.

The patient is prepared for surgery by inducing general anesthesia, establishing cardiopulmonary bypass, and inducing arrest of cardiac function. Devices and techniques for inducing arrest if cardiac function and establishing cardiopulmonary bypass are described in co-pending application Ser. Nos. 08/282,192, filed Jul. 28, 1994 now U.S. Pat. No. 5,584,803, 08/159,815, filed Nov. 30, 1993, and 08/173,899 now U.S. Pat. No. 5,433,700, filed Dec. 27, 1993 now U.S. Pat. No. 5,425,705, which are incorporated herein by reference. After general anesthesia is induced, cardiopulmonary bypass is initiated by placing a venous cannula in a major peripheral vein, such as a femoral vein, and placing an arterial cannula in a major peripheral artery, such a femoral artery. The venous and arterial cannulae are connected to a cardiopulmonary bypass system which includes an oxygenator for oxygenating blood withdrawn from the patient through the venous cannula, a filter for removing emboli from the blood, and a pump for returning the blood to the patient's arterial system through the arterial cannula.

With cardiopulmonary bypass established, cardiac function is arrested. Although conventional, open-chest, external aortic cross clamping and aortic cannulation through the aortic wall may be utilized, closed-chest clamping and cardioplegia delivery techniques are preferred. As described in the aforementioned copending applications, arrest of cardiac function may be induced on a patient by introducing an aortic catheter into a femoral artery or other major peripheral artery, transluminally positioning the distal end of the aortic catheter in the ascending aorta, and expanding the occluding member 110 (FIG. 13) to occlude the ascending aortic lumen between the coronary ostia and the brachiocephalic artery. A cardioplegic agent, preferably a potassium chloride solution mixed with blood, is delivered through a lumen of the aortic catheter into the ascending aorta where the cardioplegic fluid flows into the coronary arteries thereby perfusing the myocardium and arresting cardiac function. A venting catheter may be introduced into the right side of the heart or into the pulmonary artery from a peripheral vein, as described in copending application Ser. No. 08/415,238, filed Mar. 30, 1995 now abandoned, which is incorporated herein by reference. In addition, a retrograde cardioplegia catheter may be introduced from another peripheral vein into the coronary sinus for retrograde delivery of cardioplegic fluid through the coronary sinus. In order to obtain access to the heart from the right lateral side of the chest, the right lung is collapsed by inserting an endotracheal tube into the right main stem bronchus and applying a vacuum to deflate the lung. When requiring access to the left lateral side of the chest, when using for the vent needle 34 for example, the left lung is also collapsed.

With cardiac function arrested and the patient's circulation supported by extracorporeal cardiopulmonary bypass, the patient is ready for a medical procedure such as a mitral valve repair or replacement. Referring to FIG. 1, the instrument delivery members 2 and 6–10 are positioned in the chest to provide access into the chest cavity. In most cases, two to six instrument delivery members 2, 6–10 are required. The instrument delivery members 2, 6–10 are configured for placement within an intercostal space without requiring significant retraction of the ribs. To introduce the instrument delivery members 2, 6–10 a small puncture or incision is made in the intercostal space at the desired location and, with an obturator positioned therein, the instrument delivery members 2, 6–10 are advanced through the puncture or incision.

With the instrument delivery members 2, 6–10 in position, surgery may begin. Much, if not all, of the procedure may be carried out under direct vision by illuminating the chest cavity with a light source or light guide positioned in one of the instrument delivery members. A fiberoptic bundle may also be attached to or embedded in the wall of one of instrument delivery members to transmit light into the chest from a light source outside the chest in the manner disclosed in copending application Ser. No. 08/227,366, filed Apr. 13, 1994 now U.S. Pat. No. 5,588,949, which is incorporated herein by reference. In most cases, however, it will be desirable to use the thoracoscope 14 to provide illumination and visualization of the chest cavity, preferably by means of a video camera mounted to thoracoscope 14, which transmits a video image to the monitor 16 (FIG. 1). The thoracoscope 14 may be a rigid thoracoscope with a straight end or an angled end such as those available from Olympus Corp., Medical Instruments Division, Lake Success, N.Y. Alternatively, a thoracoscope with an articulated end steerable by means of an actuator at the proximal end of the device may be used, such as the Welch Allyn DistalVu™ (formerly Baxter DistalCam™ 360), available from Welch Allyn, Inc., of Skaneateles Falls, N.Y.

Thoracoscopic surgical instruments are then introduced to form an opening in the pericardium. Thoracoscopic scissors and graspers are then used to cut an opening in the pericardium. With an opening formed in the pericardium, the right lateral wall of the left atrium is in a direct line of sight from the right lateral chest looking through inner lumen of instrument delivery member 2.

At this time the heart is ready to be opened at an atriotomy incision in the left atrial wall between and just anterior to the pulmonary veins PV. Before making the atriotomy incision, the patient's thoracic cavity is preferably flooded with gas using the instrument delivery members 2, 2A or 2B so that the likelihood the chest cavity is filled with the gas rather than air. The control system 28 is activated and gas, such as carbon dioxide, is introduced into the patient's thoracic cavity through the instrument delivery members 2, 2A or 2B and the temperature, pressure, humidity and gas concentration are monitored by sensors 13 and fed back to the control system 28. The vacuum pump 30 may be used to remove air during the initial flooding or throughout the procedure. Alternatively, one of the instrument delivery member plugs 19 may be removed so that air is initially ejected through one of the instrument delivery members 6–10. If a gas shield is provided, the compressor, blower or fan is activated so that the gas shield passes across the throughhole 4 of the instrument delivery members 2, 2A or 2B.

If the instrument delivery member is not being used for introduction of instruments, the second plug 62 is positioned in the throughhole 4 to prevent gas losses through the throughhole 4. The gas shield provided by instrument delivery member 2B also prevent gas losses from the thoracic cavity.

The control system 28 automatically adjusts the temperature, gas flow rate, humidity, pressure and gas concentrations to maintain predetermined levels. The operator of the gas delivery system 24 monitors the display 152 and may manually control the various elements of the gas delivery system 24 rather than permitting automatic adjustment. The operator may, of course, also change the predetermined levels for any of the parameters during the procedure. A gas flow rate of 6.0 l/min has been found to provide a 90% carbon dioxide concentration in a model.

When the conditions in the patient's thoracic cavity are acceptable, such as the gas concentration, temperature, pressure, and humidity, the surgeon cuts the heart to form the atriotomy. The endoscopic atrial retractor 12 is positioned in atriotomy AI and pulled anteriorly to retract atriotomy AI open. With atriotomy AI retracted, direct visualization of mitral valve MV is possible through the instrument delivery member 2, 2A, or 2B.

Under either direct visualization or video-based viewing using the thoracoscope 14 and monitor 16, the condition of mitral valve MV is then assessed to determine whether the valve may be repaired or whether replacement is necessary. If the surgeon determines that repair is suitable, a number of repair procedures may be performed including annuloplasty, in which an annuloplasty ring is attached around the native valve to contract the annulus, quadrangular resection, in which a portion of a valve leaflet is excised and the remaining portions of the leaflet are sewn back together, commissurotomy, in which the valve commissures are incised to separate the valve leaflets, shortening of the chordae tendonae, reattachment of severed chordae tendonae or papillary muscle tissue, and decalcification of the valve leaflets or annulus. Several of these procedures may be performed on the same valve. In particular, annuloplasty rings may be used in conjunction with any repair procedures where contracting or stabilizing the valve annulus is desirable.

If none of the repair procedures will adequately treat the diseased valve, the native valve is replaced with the replacement valve 20. The techniques for introducing and securing the replacement valve within the heart will be analogous to those described above for annuloplasty ring, and are further described in copending application Ser. No. 08/281,962, filed Jul. 28, 1994 now abandoned, which is incorporated herein by reference. Once a prosthetic valve of the appropriate size is identified, the valve is attached to the valve annulus.

When the annuloplasty ring or replacement valve has been secured within the heart, the atriotomy AI is ready for closure. Before, during and even after closure of the atriotomy, the heart is preferably vented to remove gas from the heart. Before filling the heart with blood, a surfactant, such as the phospholipid pulmonary surfactant found in the lung, may be introduced into the thoracic cavity. Furthermore, the amount of retained air or gas may be observed using transesophageal echocardiography (TEE). A description of using TEE for locating retained air in the heart is disclosed in Orihashi et al. "Retained Intracardiac Air in Open Heart Operations Examined by Transesophageal Echocardiography", Ann Thorac Surg 55:1467–71 (1993) and Oka et al. "Detection of Air Emboli in the Left Heart by M-Mode Transesophageal Echocardiography Following Cardiopulmonary Bypass," Anesthesiology 63(1):109-3 (1985), which are incorporated herein by reference.

Figure 17:
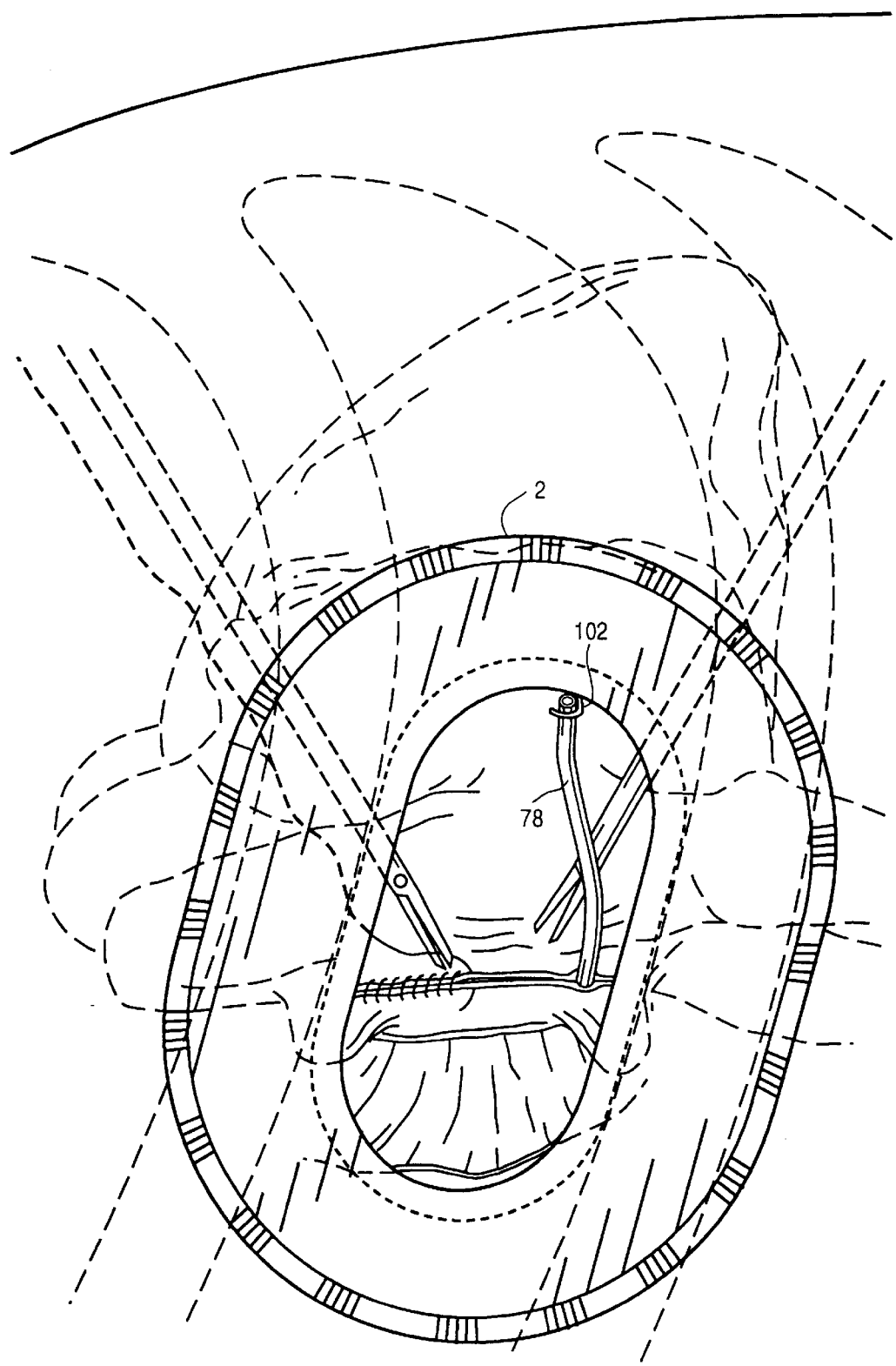
FIG. 17 is a view looking through the instrument delivery member with an atriotomy being closed and a vent extending through the atriotomy.

The needle vent 34, vent 78 and/or left ventricle vent 104 are positioned in the left ventricle and the aortic vent 106 is positioned in the ascending aorta. The needle vent 34 preferably has a manually manipulatable bulb (not shown) for withdrawing gas from the left ventricle. Alternatively, the needle vent 34 may be coupled to the vacuum pump 30. Referring to FIG. 17, the vent 38 is preferably positioned through the replacement valve, or through the native mitral valve, when a repair is performed, so that the left ventricle can be flood with a gas, such as carbon dioxide, and vented before atriotomy closure.

Before removing gas in the left ventricle, gas in the ascending aorta is preferably vented using the aortic vent 106. The patient is tilted feet downward so that gas in the left ventricle and ascending aorta migrates toward the occluding member 110. The aortic vent 106 is then used to vent gas around the ascending aorta. Referring to FIG. 13, the aortic vent 106 is preferably rotated so that the opening 114 circumscribes the occluding member 110 between the occluding member 110 and the aortic lumen. Although it is preferred to provide both the aortic vent 106 and left ventricle vent 104, both the aorta and left ventricle may be vented with the same catheter. The heart is preferably mechanically manipulated during venting of the various chambers in the heart in a manner similar to the open-chest procedures except that the mechanical manipulators extend through the instrument delivery members 2, 6–10. A discussion of conventional de-airing procedures is described in Taber et al. "Prevention of air embolism during open-heart surgery: A study of the role of trapped air in the left ventricle" *Surgery* 68(4):685–691 (1970) and van der Linden and Casimir-Ahn, "When Do Cerebral Emboli Appear During Open Heart Operations? A Transcranial Doppler Study," *Ann Thorac Surg* 51:237–41 (1991) which are incorporated herein by reference.

After removing gasses from the ascending aorta, the patient is then tilted head downward so that gas in the left ventricle rises to the apex where the gas can be removed using the needle vent 34, vent 78 or left ventricle vent 104. The gas at the apex of the left ventricle is then vented. When using the needle vent 34, the needle vent 34 is preferably moved to various other locations in the heart where pooled air may be a problem or where ultrasound or fluoroscopy have identified pooled air or gas. Other locations where the needle vent may be used include the right upper pulmonary vein, the right coronary sinus of Valsalva, the left atrial appendage, which may be also be inverted or closed with sutures, and the left upper pulmonary vein.

The atriotomy is then preferably closed using thoracoscopic needle drivers and a curved needle on a suture. Alternatively, an endoscopic stapling device such as an AutoSuture™ Powered Multifire Endo TA60, available from United States Surgical Corp. of Norwalk, Conn., or an endoscopic fascia stapler, may be inserted through an anterior instrument port and positioned around atriotomy AI to drive a series of staples into the atrial wall to close the atriotomy. The opening formed in the pericardium may be closed with sutures or staples in a manner similar to that used for closing atriotomy AI. However, in most cases, closure of the pericardium is not necessary, and the opening may be left without adverse effect.

To complete the operation, cardiac function is then restored by discontinuing delivery of cardioplegic fluid, terminating occlusion of the ascending aortic lumen, and perfusing the myocardium with warm blood. When the occluding member 110 is used, the occluding member 110 is deflated and warm blood is allowed to flow into the coronary arteries. If sinus rhythm does not return immediately, electrical defibrillation is used to stimulate the heart and/or pacing leads may be used to pace the heart for a period of time. Once the heart is beating normally, the aortic catheter is removed from the patient along with any venting catheters or retrograde cardioplegia delivery catheter which may have been used. Chest tubes may be inserted into the chest to provide drainage. The patient is then weaned from cardiopulmonary bypass, and the arterial and venous cannulae are removed from the patient.

Another preferred method of minimizing the risk of air embolism is now described. The method described above generally provides a gas, such as carbon dioxide, when the heart is initially opened so that air cannot enter the heart during the procedure. As an alternative, the gas may be injected into the patient when the first instrument delivery member 2, 6–10 is inserted into the patient. In this manner, air is prevented from entering the thoracic cavity throughout the procedure.

In yet another preferred method, the gas may be used to displace air in the thoracic cavity and the heart just before the atriotomy is closed. The gas may be introduced through the instrument delivery member 2, 2A or 2B, vent 78, or needle vent 34. When using the vent 78, the vacuum pump 30 may be used to withdraw air which is displaced by the gas. The gas concentration is monitored so that the gas concentration is at an acceptable level before closing the atriotomy. In this manner, the amount of time the thoracic cavity is exposed to the gas is minimized.

Figure 18:
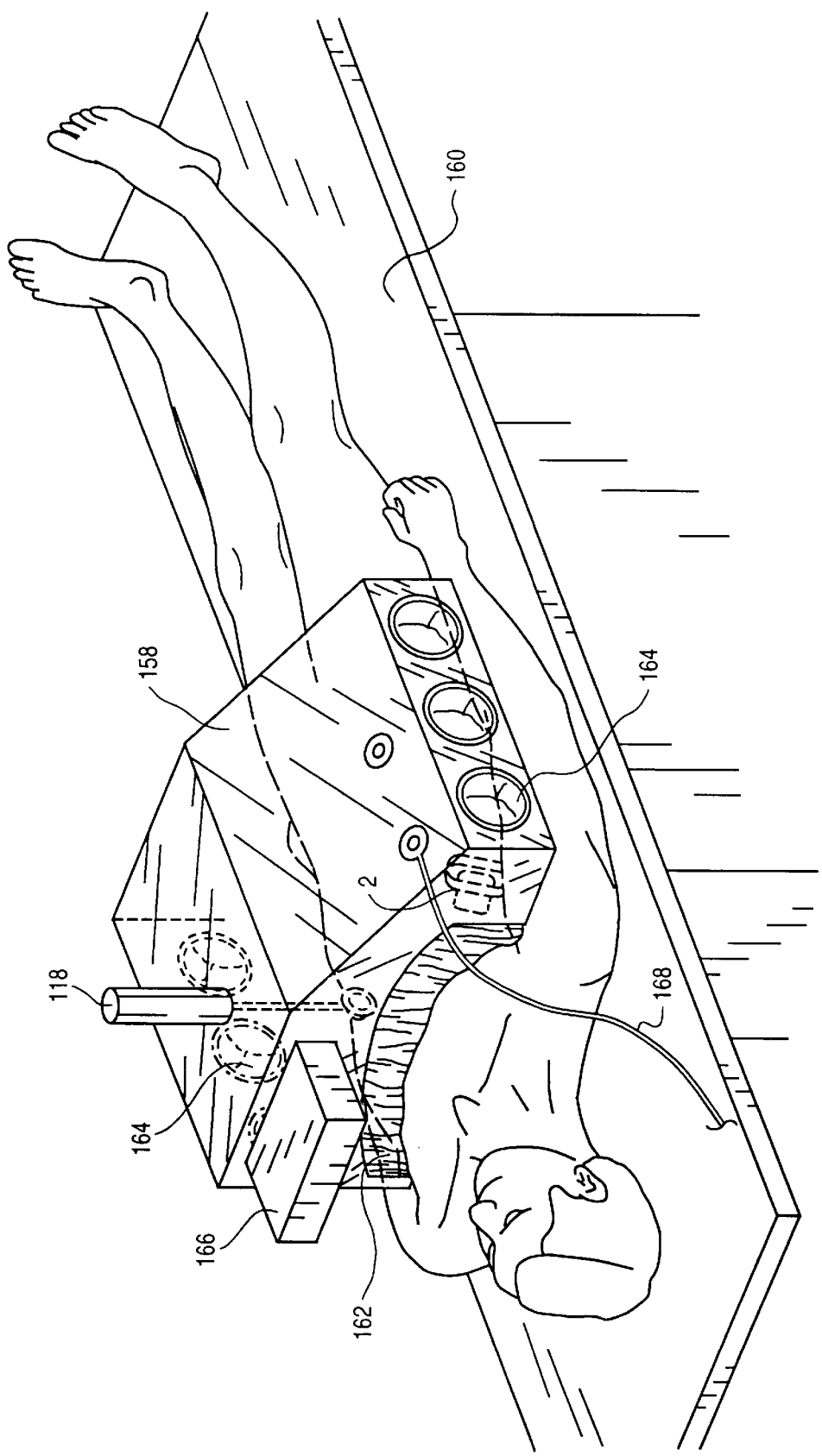
FIG. 18 is an isometric view of an enclosure extending around a patient.

Referring to FIG. 18, another embodiment of an apparatus for preventing air embolism when performing a procedure in a patient's thoracic cavity is shown. An enclosure 158 extends around the patient and is supported by an operating table 160. A drape 162 extends around the patient's chest and provides a substantially air-tight seal. The drape 162 may include an adhesive strip (not shown) for forming the substantially air-tight seal. The enclosure 158 includes a number of arm pass-throughs 164 on both sides of the enclosure 158. The arm pass-throughs 164 are substantially air tight and permit the surgeon to perform procedures in the enclosure. A tool box 166 is slidably coupled to the exterior of the enclosure 158 for passing tools into the enclosure 158. An advantage of the enclosure 158 is that a retractor 118 may be mounted to the enclosure 158. The enclosure 158 is preferably coupled to the gas delivery system 24 and control system 26 described above in connection with the previously disclosed embodiments via a line 168. The enclosure 158 is particularly useful when providing a pressure in the enclosure 158 which is higher than the pressure outside the enclosure 158 so that air does not enter the enclosure 158. The enclosure 158 also minimizes the amount of gas which is released into the operating room so that surgeon exposure to the gas is minimized.

It is understood that while the invention has been described specifically in the context of mitral valve repair and replacement, the devices and methods disclosed herein will have equal application to a number of other procedures on a patient's cardiovascular system. Furthermore, the preferred embodiments are developed as merely preferred embodiments of the invention and modifications may be made which fall within the scope of the invention as defined by the claims. For example, the gas outlets may be angled toward the proximal end with baffles to redirect the gas toward the distal end, the gas outlets which pass across the throughhole may contact a baffle which directs the gas toward the distal end, the gas outlet may simply be a hose which is clipped to the sidewall or any other part of the instrument delivery member so long as the gas outlet is coupled to the remainder of the instrument delivery member, and the left ventricular vent may include only one lumen rather than two. In addition, although it is preferred to place the patient on cardiopulmonary bypass when performing procedures the present invention is equally applicable to procedures in which the patient's heart is not stopped. Therefore, the above description should not be taken as limiting the scope of the invention which is defined by the claims.

What is claimed is:

1. A method of minimizing the risk of air emboli in a patient's circulatory system when performing a procedure in the patient's thoracic cavity, comprising the steps of:

inserting an instrument delivery member into a patient's thoracic caviler thereby forming a first percutaneous penetration, the instrument delivery member having a throughhole sized to permit an instrument to pass therethrough;

coupling an outlet from a source of gas to the instrument delivery member;

injecting the gas from the source of gas into the patient's thoracic cavity through the outlet coupled to the instrument delivery member, the injecting step being carried out with a plurality of outlets coupled to the instrument delivery member for passing the gas into the patient's thoracic cavity, the injecting step being carried out so that the gas issuing from the plurality of outlets forms a gas shield across the throughhole.

2. The method of claim 1, further comprising the step of:

inserting an instrument for performing a procedure on the patient's heart through the first instrument delivery member.

3. The method of claim 1, wherein:

the coupling step is carried out with the source of gas being a source of carbon dioxide.

4. The method of claim 1, further comprising the step of:

withdrawing the gas through an inlet of a vacuum line, the vacuum line being coupled to a vacuum pump.

5. The method of claim 1, further comprising the step of:

monitoring a gas concentration in the patient's thoracic cavity;

the injecting step being carried out to maintain a minimum gas concentration in the patient's thoracic cavity.

6. The method of claim 1, further comprising the step of:

humidifying the gas before the injecting step.

7. The method of claim 1, further comprising the step of:

measuring a temperature in the patient's thoracic cavity; and changing the temperature of the gas injected into the patient in response to the temperature in the patient's thoracic cavity measured during the measuring step.

8. The method of claim 1, further comprising the step of:

measuring the pressure in the patient's thoracic cavity;

the injecting step being carried out so that a pressure in the patient's thoracic cavity exceeds atmospheric pressure thereby resisting introduction of air into the patient's thoracic cavity.

9. The method of claim 1, wherein:

the inserting step is carried out with the outlet being integrally formed with the instrument delivery member.

10. An instrument delivery member adapted to inject a gas into a patient's thoracic cavity to minimize the risk of air embolism, comprising:

a sidewall forming a throughhole sized and configured to permit a medical instrument to pass therethrough, the sidewall having a proximal end, a distal end and a longitudinal axis, the throughhole having a cross-section in a direction perpendicular to the longitudinal axis, the cross-section having a width and a length, at least one of the width and length being at least 2 cm;

a gas inlet configured to be coupled to a source of gas;

a plurality of gas outlets coupled to the sidewall for injecting a gas into a patient's thoracic cavity, the plurality of gas outlets being fluidly coupled to the gas inlet, the plurality of gas outlets being positioned and configured to direct a gas shield across substantially the entire throughhole so that gas losses through the throughhole are minimized.

* * * * *